United States Patent [19]
Kuhn et al.

[11] Patent Number: 5,773,227
[45] Date of Patent: Jun. 30, 1998

[54] BIFUNCTIONAL CHELATING POLYSACCHARIDES

[75] Inventors: Michael A. Kuhn, Eugene, Oreg.; Tobias Meyer, Durham, N.C.; Nancy L. Allbritton, Menlo Park, Calif.

[73] Assignee: Molecular Probes, Inc., Eugene, Oreg.

[21] Appl. No.: 82,269

[22] Filed: Jun. 23, 1993

[51] Int. Cl.$^6$ .................. G01N 33/566; C07K 17/10; C08B 37/02
[52] U.S. Cl. .................. 435/7.21; 435/7.2; 530/300; 530/345; 536/45; 536/46; 536/81; 536/56; 536/112
[58] Field of Search .................. 530/300, 345; 435/7.1, 7.2, 7.21; 536/1.11, 45, 46, 56, 51, 112

[56] References Cited

U.S. PATENT DOCUMENTS

| | | | |
|---|---|---|---|
| 4,603,209 | 7/1986 | Tsien et al. | 548/236 |
| 4,849,362 | 7/1989 | DeMarinis et al. | 436/63 |
| 4,975,532 | 12/1990 | Rowley et al. | 536/51 |
| 5,049,673 | 9/1991 | Tsien et al. | 546/107 |
| 5,094,848 | 3/1992 | Brixner | 424/85.91 |
| 5,134,232 | 7/1992 | Tsien et al. | 540/467 |
| 5,227,487 | 7/1993 | Haugland et al. | 546/15 |

FOREIGN PATENT DOCUMENTS 9301498  1/1993  WIPO .

OTHER PUBLICATIONS

Fery–Forgues, et al., New J. Chem., 14, 617 (1990).
Haugland, Handbook of Fluorescent Probes and Research Chemicals Set 20 and 22 (1992).
DeBelder, et al.; arbohydrates Res. 30, 375 (1973).
Raju, et al. in AM. J. Physiol. 256, C540 (1989).
Glabe, et al., Analyt. Biochem., 130, 287(1983).
Gimlich et al., Develop. Biol., 109, 509 (1985).
Schlatterer, et al., Eur. J. Cell Bio., 58, 172 (1992).
Chelsky, et al., Molec. Cell Biol. 9, 2487 (1989).
Wagner, et al., FEBS Letters 275, 1 (1990).
Roise, et al., J. Biol. Chem. 263, 4509 (1988).
Haugland, Handbook of Fluorescent Probes and Research Chemicals Set 27 (1992).
Vincent, et al., Cell, 68, 923 (1992).
Garcia–Bustos, et al., Biochem. Biophys. Acta 1071, 83 (1991).
Hartl, et al., Biochim. Biophys. Acta 988, 1 (1989).
Hendrick, et al., PNAS 86, 4056 (1989).
Munro, et al., Cell 48, 899 (1987).
R. Pethig, et al., Cell Calcium 10, 491 (1989).
Tsien and Pozzan, Methods in Enzymology 172, 230 (1989).

*Primary Examiner*—Lora M. Green
*Attorney, Agent, or Firm*—Allegra J. Helfenstein; Anton E. Skaugset

[57] ABSTRACT

This invention describes bifunctional polysaccharides conjugated to both a chelating group suitable for the selective complexation of metal cations, and a targeting peptide specific for a cellular substructure. These bifunctional polysaccharides are primarily useful for the regulation, detection and quantification of metal ion levels, such as $Ca^{2+}$, $Mg^{2+}$, $Na^+$, $K^+$, or $Li^+$, in specific cellular structures. Localization within the cellular structure is accomplished by the targeting peptide, whereupon the large, water-soluble polysaccharide prevents diffusion of the chelating group from the targeted site. When the target cell structure is the nucleus of a fertilized egg cell, the polysaccharide-chelator conjugate remains sequestered within the nucleus until the breakdown of the nuclear envelope, whereupon the reagent becomes sequestered into both daughter nuclei. This means of tracking daughter cells is practical even through several cell divisions.

17 Claims, 12 Drawing Sheets

XII.

1) NH$_2$-DEXTRAN/DMSO
2) KOH (aq.) pH 12

XIII.

1.)
2.) NLS; pH 7.0

XIV.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 13 AMINO ACIDS
        ( B ) TYPE: Amino Acid
        ( D ) TOPOLOGY: Linear ( i i ) MOLECULE TYPE: Peptide
        ( A ) DESCRIPTION:

( i i i ) HYPOTHETICAL: no ( v ) FRAGMENT TYPE:

( x ) PUBLICATION INFORMATION:
        ( A ) AUTHORS: Vincent, Jean-Paul and O'Farrell, Patrick H.
        ( B ) TITLE: The State of Engrailed Expression is not Clonally
            Transmitted during Early Drosophila Development
        ( C ) JOURNAL: Cell
        ( D ) VOLUME: 68
        ( E ) ISSUE: 6 March 1992
        ( F ) PAGES: 923-931

( x i ) SEQUENCE DESCRIPTION: SEQ ID NO:1:

Cys Gly Tyr Gly Val Ser Arg Lys Arg Pro Arg Pro Gly
1                    5                           10

( 2 ) INFORMATION FOR SEQ ID NO:2:

( i ) SEQUENCE CHARACTERISTICS:
        ( A ) LENGTH: 11 AMINO ACIDS
        ( B ) TYPE: Amino Acid
        ( D ) TOPOLOGY: Linear ( i i ) MOLECULE TYPE: Peptide ( i i i ) HYPOTHETICAL: no ( v ) FRAGMENT TYPE:

( x ) PUBLICATION INFORMATION:
        ( A ) AUTHORS: Chelsky, Daniel, Ralph, Rebecca and Jonak, Gerald
        ( B ) TITLE: Sequence Requirements for Synthetic Peptide-
            Mediated Translocation to the Nucleus
        ( C ) JOURNAL: Molecular and Cellular Biology
        ( D ) VOLUME: 9
        ( E ) ISSUE: 6
        ( F ) PAGES: 2487-2492
        ( G ) DATE: 1989

( x i ) SEQUENCE DESCRIPTION: SEQ ID NO:2:

Cys Gly Gly Pro Lys Lys Lys Arg Lys Val Gly (2) INFORMATION FOR SEQ ID NO:3:

(i) SEQUENCE CHARACTERISTICS:
        (A) LENGTH: 10 AMINO ACIDS
        (B) TYPE: Amino Acid
        (D) TOPOLOGY: Linear (ii) MOLECULE TYPE: Peptide (iii) HYPOTHETICAL: no (v) FRAGMENT TYPE:

(ix) FEATURE:
        (D) OTHER INFORMATION: Xaa at position 3 is the modified amino acid ornithine.

(x) PUBLICATION INFORMATION:
        (A) AUTHORS: Chelsky, Daniel, Ralph, Rebecca and Jonak, Gerald
        (B) TITLE: Sequence Requirements for Synthetic Peptide-Mediated Translocation to the Nucleus
        (C) JOURNAL: Molecular and Cellular Biology
        (D) VOLUME: 9
        (E) ISSUE: 6
        (F) PAGES: 2487-2492
        (G) DATE: 1989

(xi) SEQUENCE DESCRIPTION: SEQ ID NO:3:

Cys Gly Xaa Ala Lys Lys Lys Lys Leu Asp
1            5                  10

(2) INFORMATION FOR SEQ ID NO:4:

(i) SEQUENCE CHARACTERISTICS:
        (A) LENGTH: 14 AMINO ACIDS
        (B) TYPE: Amino Acid
        (D) TOPOLOGY: Linear (ii) MOLECULE TYPE: Peptide (iii) HYPOTHETICAL: no (v) FRAGMENT TYPE:

(x) PUBLICATION INFORMATION:
        (A) AUTHORS: Chelsky, Daniel, Ralph, Rebecca and Jonak, Gerald
        (B) TITLE: Sequence Requirements for Synthetic Peptide-Mediated Translocation to the Nucleus
        (C) JOURNAL: Molecular and Cellular Biology
        (D) VOLUME: 9
        (E) ISSUE: 6
        (F) PAGES: 2487-2492
        (G) DATE: 1989

(xi) SEQUENCE DESCRIPTION: SEQ ID NO:4:

Cys Val Arg Thr Thr Lys Gly Lys Arg Lys Arg Ile Asp Val
1            5                  10

(2) INFORMATION FOR SEQ ID NO:5:

(i) SEQUENCE CHARACTERISTICS:
        (A) LENGTH: 11 AMINO ACIDS
        (B) TYPE: Amino Acid
        (D) TOPOLOGY: Linear (ii) MOLECULE TYPE: Peptide (iii) HYPOTHETICAL: no (v) FRAGMENT TYPE:

(x) PUBLICATION INFORMATION:
        (A) AUTHORS: Chelsky, Daniel, Ralph, Rebecca and Jonak, Gerald (B) TITLE: Sequence Requirements for Synthetic Peptide-
Mediated Translocation to the Nucleus
(C) JOURNAL: Molecular and Cellular Biology
(D) VOLUME: 9
(E) ISSUE: 6
(F) PAGES: 2487-2492
(G) DATE: 1989

(xi) SEQUENCE DESCRIPTION: SEQ ID NO:5:

```
Cys Gly Gly Leu Ser Ser Lys Arg Pro Arg Pro
1               5                       10
```

(2) INFORMATION FOR SEQ ID NO:6:

(i) SEQUENCE CHARACTERISTICS:
(A) LENGTH: 6 AMINO ACIDS
(B) TYPE: Amino Acid
(D) TOPOLOGY: Linear (ii) MOLECULE TYPE: Peptide (iii) HYPOTHETICAL: no (v) FRAGMENT TYPE:

(ix) FEATURE:
(D) OTHER INFORMATION: R-Xaa-(F)-Xaa- Xaa-(S) within the
amino- terminal 50 amino acids, where R = Arg; Xaa =
other amino acid; (F) in location three (3) can be
phenylalanine, leucine, valine, or isoleucine; and S in
location six (6) can be serine, threonine, or glycine.

(x) PUBLICATION INFORMATION:
(A) AUTHORS: Hendrick, Joseph P., Hodges, Peter E., Rosenberg,
Leon E.
(B) TITLE: Survey of Amino-terminal Proteolytic Cleavage
Sites in Mitochondrial Precursor Proteins: Leader
Peptides Cleaved By Two Matrix Proteases Share a Three-
amino Acid Motif
(C) JOURNAL: Proceedings of the National Academy of Sciences
(D) VOLUME: 86
(E) ISSUE: June 1989
(F) PAGES: 4056-4060
(G) DATE: 1989

(xi) SEQUENCE DESCRIPTION: SEQ ID NO:6:

```
Arg Xaa Phe Xaa Xaa Ser
1               5
```

(2) INFORMATION FOR SEQ ID NO:7:

(i) SEQUENCE CHARACTERISTICS:
(A) LENGTH: 4 AMINO ACIDS
(B) TYPE: Amino Acid
(D) TOPOLOGY: Linear (ii) MOLECULE TYPE: Peptide (iii) HYPOTHETICAL: no (v) FRAGMENT TYPE:

(x) PUBLICATION INFORMATION:
(A) AUTHORS: Munro, Sean and Pelham Hugh, R.B.
(B) TITLE: A C-Terminal Signal Prevents Secretion of Luminal
ER Proteins
(C) JOURNAL: Cell
(D) VOLUME: 48
(E) ISSUE: 13 March 1987
(F) PAGES: 899-907
(D) DATE: 1987

(xi) SEQUENCE DESCRIPTION: SEQ ID NO:7:

```
Lys Asp Glu Leu
```

( 2 ) INFORMATION FOR SEQ ID NO:8:

( i ) SEQUENCE CHARACTERISTICS:
        ( A ) LENGTH: 11 AMINO ACIDS
        ( B ) TYPE: Amino Acid
        ( D ) TOPOLOGY: Linear ( i i ) MOLECULE TYPE: Peptide ( i i i ) HYPOTHETICAL: no ( v ) FRAGMENT TYPE:

( x i ) SEQUENCE DESCRIPTION: SEQ ID NO:8:

```
Cys  Gly  Gly  Leu  Ser  Ser  Lys  Arg  Pro  Arg  Pro
1                   5                        10
```

( 2 ) INFORMATION FOR SEQ ID NO:9:

( i ) SEQUENCE CHARACTERISTICS:
        ( A ) LENGTH: 13 AMINO ACIDS
        ( B ) TYPE: Amino Acid
        ( D ) TOPOLOGY: Linear ( i i ) MOLECULE TYPE: Peptide ( i i i ) HYPOTHETICAL: no ( v ) FRAGMENT TYPE:

( i x ) FEATURE:
        ( D ) OTHER INFORMATION: Xaa at location 13 is glycine having
            an amide modified C-term ( x i ) SEQUENCE DESCRIPTION: SEQ ID NO:9:

```
Cys  Gly  Tyr  Gly  Val  Ser  Arg  Lys  Arg  Pro  Arg  Pro  Xaa
1                   5                        10
```

BIFUNCTIONAL CHELATING POLYSACCHARIDES

FIELD OF THE INVENTION

This invention relates to bifunctional polysaccharides that are chelators for monovalent and divalent metal cations. Specifically, this invention describes water soluble polysaccharides that are covalently bound to a targeting peptide and a fluorescent or nonfluorescent chelator, for use in detecting, regulating, and/or quantifying mono- and divalent metal cations in living cells.

BACKGROUND OF THE INVENTION

The detection, quantification and regulation of metal ion levels in biological systems is of great importance, due to the important role of metals in many processes, including enzyme regulation, determination of protein structure, and cellular signaling. Chelating compounds bind selectively to specific ions. If the chelating compound incorporates a fluorescent or fluorogenic moiety, the fluorescent signal that is generated in response to the presence of the ion acts as an indicator for the presence and/or amount of ion present.

Chelating indicators for alkali metals ions such $Na^+$, $K^+$, and $Li^+$ usually incorporate a crown ether as the binding moiety. Benzofuranyl indicators for alkali metal ions comprising an aza crown ether attached to one or two fluorophores are described by Tsien, et al. in U.S. Pat. No. 5,134,232 (1992) for intracellular use. A fluorescent N-phenyl-monoaza crown ether containing a benzoxazinone fluorophore (BOZ-crown) or a merocyanine laser dye (DCM-crown) is described by Fery-Forgues, et al., NEW J. CHEM., 14, 617 (1990); these dyes, however, are not compatible with use in aqueous media. Crown ethers bound to benzofuranyl indicators are further described in Haugland, HANDBOOK OF FLUORESCENT PROBES AND RESEARCH CHEMICALS Set 22 (1992) (incorporated by reference).

There are a variety of chelating indicators that make use of poly-carboxylate binding sites to selectively bind metal cations. Some indicators that are based on the BAPTA chelate (1,2-bis-(2-aminophenoxyethane)-N,N,N',N'-tetraacetic acid) have shown high selectivity for calcium ions inside cells. Some of these indicators are quin-2, fura-2, indo-1 (U.S. Pat. No. 4,603,209 to Tsien, et al. (1986)); fluo-3 and rhod-2 (U.S. Pat. No. 5,049,673 to Tsien, et al. (1991)); and FURA RED™ (Molecular Probes, Inc., Eugene, Oreg, trademark for 1-[6-amino-2-2-(5-oxo-2-thioxo-4-thiazolidinylidene methyl-5-benzofuranyloxyl]-2-(2'-2-amino-5'-methyl-phenoxy) ethane N, N, N', N'-tetraacetic acid and the tetraacetyloxymethyl ester thereof, as described in U.S. Pat. No. 4,849,362 to De Marinis, et al. (1989)). A family of BAPTA-based indicators that are selective for calcium ions (Calcium Green, Calcium Orange and Calcium Crimson) have been described HANDBOOK OF FLUORESCENT PROBES AND RESEARCH CHEMICALS, supra, Set 20 (incorporated by reference).

The fluorescent indicator furaptra is based upon o-aminophenoltriacetic acid (APTRA), a tricarboxylic chelator which is strongly selective for $Mg^{2+}$ ions, was described by Raju, et al. in AM. J. PHYSIOL. 256, C540 (1989). Furaptra and other APTRA-based $Mg^{2+}$ indicators (mag-fura-2, mag-fura-5, mag-indo-1), which are similar in properties to the above mentioned BAPTA-based calcium indicators are described in HANDBOOK OF FLUORESCENT PROBES AND RESEARCH CHEMICALS, supra, Sets 20 & 22.

While there are many fluorescent indicators that have been determined to be effective and highly selective for certain ions, they share some common drawbacks. Because of negative charges on the chelating compounds, these low molecular weight compounds tend to bind to intracellular proteins, altering their metal binding properties. In addition, due to their relatively small size, they are readily sequestered non-selectively in intracellular vesicles, further limiting their effectiveness. One means of circumventing these problems is to attach the desired indicator to a large, water-soluble polysaccharide, such as dextran or ficol, by means of modification of the polysaccharide to allow covalent attachment of the indicator. Dextrans and ficols are especially suitable for this application, as they are low cost, optically transparent above about 250 nm and available in multiple ranges of molecular weights. Furthermore, polysaccharides and their conjugates are reasonably compatible with most biological materials and do not interact significantly with intracellular components. Although the literature includes descriptions of derivatives of polysaccharides, including dextrans, that are bound to fluorescent dyes (DeBelder et al.; CARBOHYDRATE RES. 30, 375 (1973); Glabem et al., ANALYT. BIOCHEM. 130, 287 (1983); Gimlich et al., DEVELOP. BIOL., 109, 509 (1985)), the fluorescent polysaccharides described in these references do not possess the ability to react selectively with metal ions.

The coupling of the fluorescent calcium indicator fura-2 with a dextran has been described (Schlatterer, et al., EUR. J. CELL BIO., 58, 172 (1992). The dextran was used to overcome the tendency of free fura-2 to sequester and compartmentalize within cells, taking advantage of dextran's lack of interaction with intracellular components. A series of fluorescent ion-selective diaryldiaza crown ether conjugates, including polysaccharides, sold by Molecular Probes, Inc., Eugene, Oreg, is described in U.S. Pat. No. 5,405,975 to Kuhn et al. (1995) (incorporated by reference). Similarly, a series of BAPTA based ion selective indicators that incorporate reactive sites or are covalently attached to polymolecular assemblies (including polysaccharides) for sale from Molecular Probes, Inc., is described in U.S. Pat No. 5,453,517 to Kuhn et al. (1995) (incorporated by reference). In contrast to the compounds of the invention, the indicator conjugates described above that are not functionalized by a targeting sequence, are designed to prevent localization in cellular substructures.

Nevertheless, there is a need for chelating materials that can be targeted for compartmentalization in a specific cellular organelle so that ion levels can be monitored in a cellular microenvironment. By attaching a peptide to the chelate-bound polysaccharide, the peptide serves as a targeting sequence that guides the polysaccharide-conjugate to a specific location within the cell where the peptide is recognized by the specific receptor site for which it is synthesized, and the entire polysaccharide assembly is drawn across the intracellular membrane by a cell-mediated mechanism. Once the membrane has been crossed, the large polysaccharide keeps the chelator from diffusing back out of the target area. This reagent therefore allows specific sites within a cell to be analyzed for metal ion levels, and the concentration of metal ions in specific cellular substructures to be selectively buffered. An added and important advantage in the case of nuclear targeted bifunctional polysaccharides is that upon cell division, the polysaccharides resequester into the nuclei of both daughter cells.

Although the existence of targeting sequences for a number of intracellular organelles have previously been described, e.g. Chelsky, et al., MOLEC. CELL BIOL. 9, 2487 (1989) and Wagner, et al., FEBS LETTERS 275, 1 (1990) (nuclear localization sequences); Roise et al., J. BIOL. CHEM 263, 4509 (1988) (mitochondrial matrix targeting sequences, ER targeting sequences); the attachment of such peptides to polysaccharides for use in localization of a chelator for metal ions in a subcellular compartment has not previously been described.

Polysaccharides that simultaneously contain fluorescent dyes and a second functional group that includes amines, epoxides, thiols, maleimides, iodoacetamides and carboxylic acids have been described in Bimlich et al., DEVELOP. BIOL. 109, 509 (1985); and Haugland, HANDBOOK OF FLUORESCENT PROBES AND RESEARCH CHEMICALS Set 27 (1992). These materials, however, do not contain a chelator for metal ions nor do they contain a targeting sequence to localize in specific cellular substructures.

A method to derivatize dextran to link a detectable label to an immunospecific substance such as an antigen or antibody is described in U.S. Pat. No. 4,975,532 to Rowley et al. (1990). The patent includes several examples of dextrans bound to both a specific reaction partner and a fluorescent label. However, the fluorescent labels that are described in the Rowley reference are not capable of acting as indicators for metal ions. Furthermore, the specific reaction partners described by Rowley et al. are used to accomplish direct or competitive binding assays and there is no indication that the materials could be modified to provide for targeting specific regions or substructures within a cell.

A bifunctional dextran bound to both a caged fluorescein and a nuclear localization peptide is described by Vincent et al., CELL, 68, 923 (1992). The caged fluorescein of the compound responds to external photoactivation to give a fluorescent signal used to trace the lineage of marked cells. The described reagent does not respond to an intracellular component and does not function as an indicator for metal ions.

SUMMARY OF THE INVENTION AND DESCRIPTION OF PREFERRED EMBODIMENTS

Figure 1:
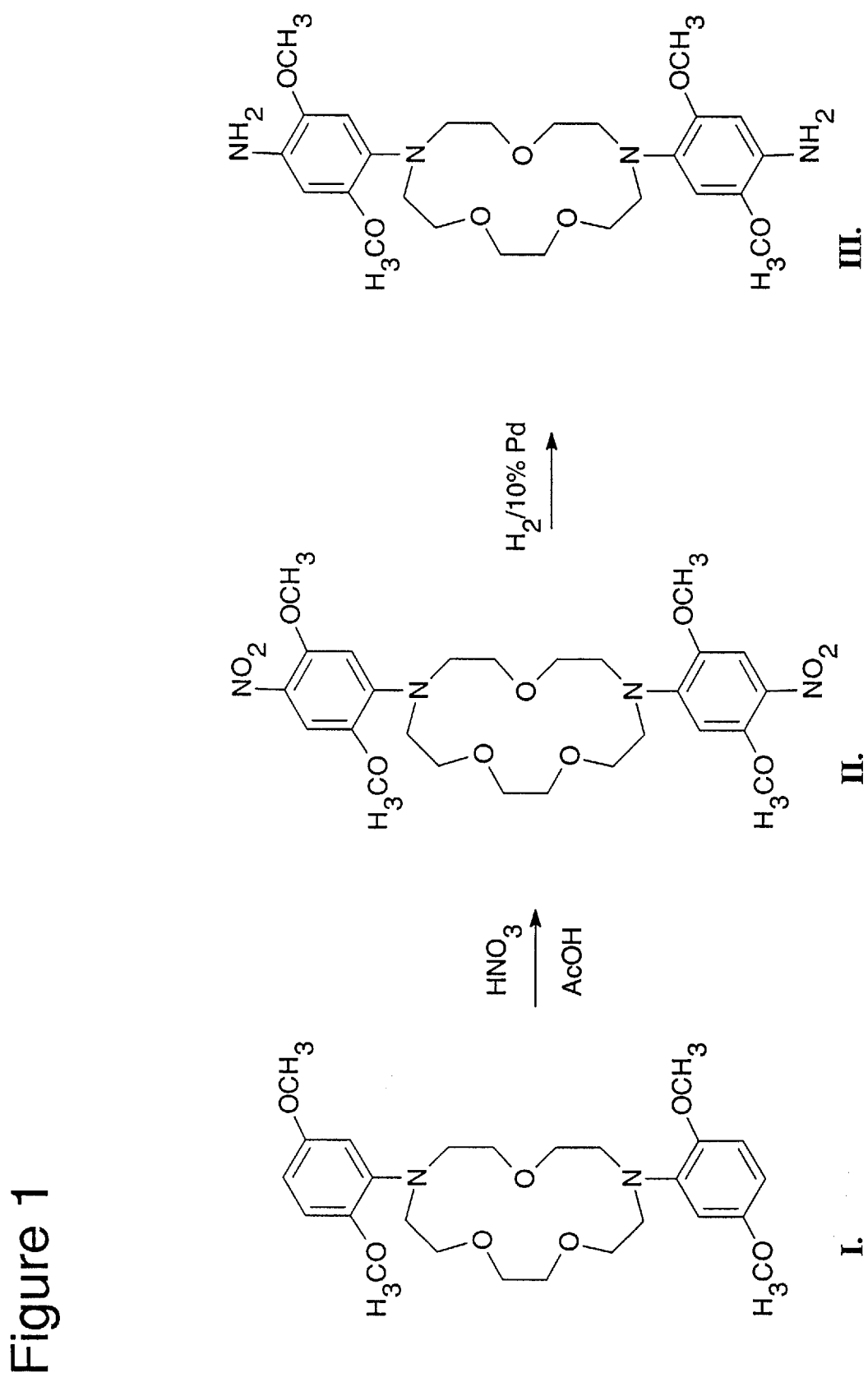
FIGS. 1 and 2: Synthetic pathway to a green fluorescent diaryldiazatrioxa crown ether conjugated to a polysaccharide.
Figure 2:
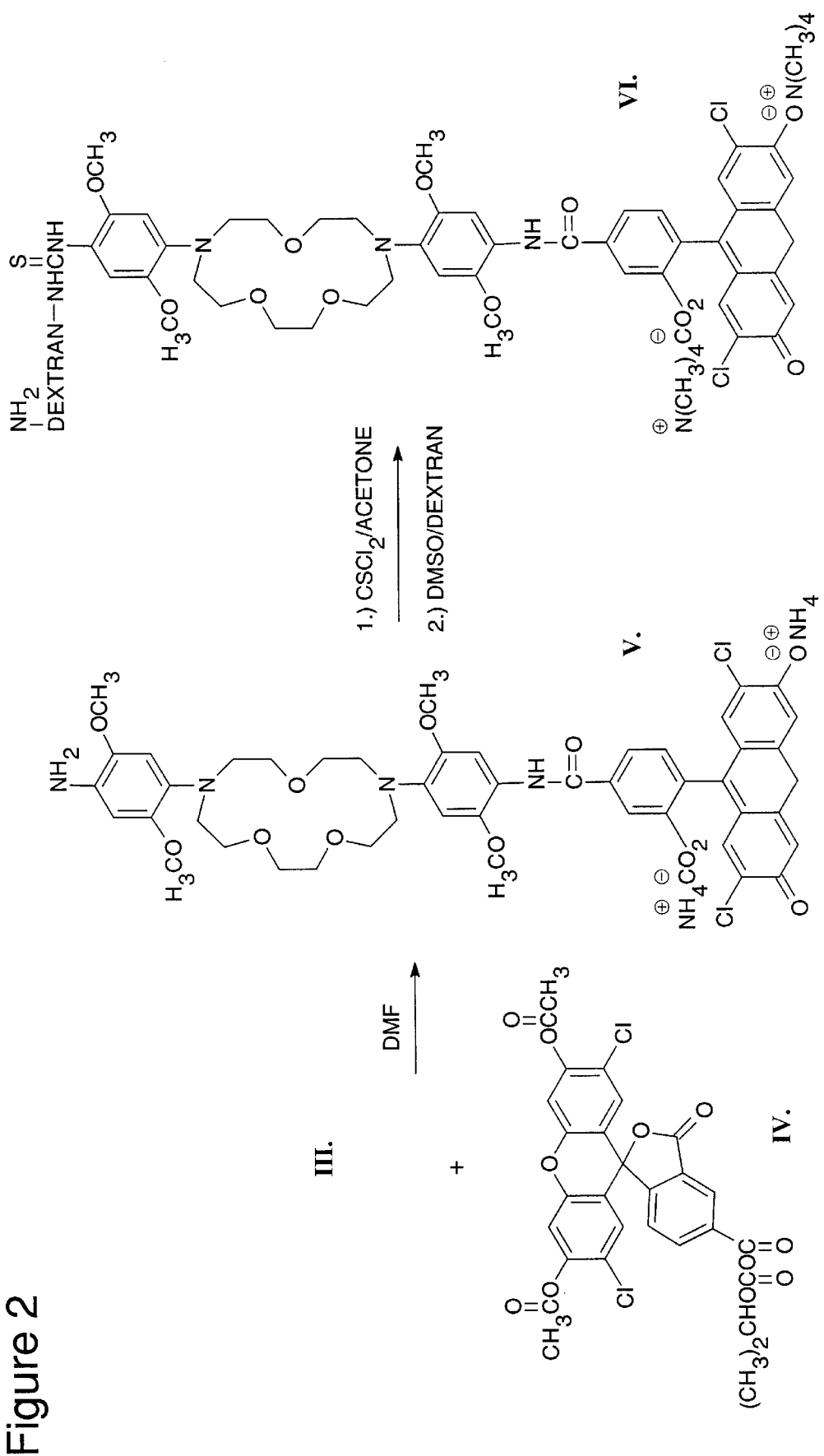
Figure 3:
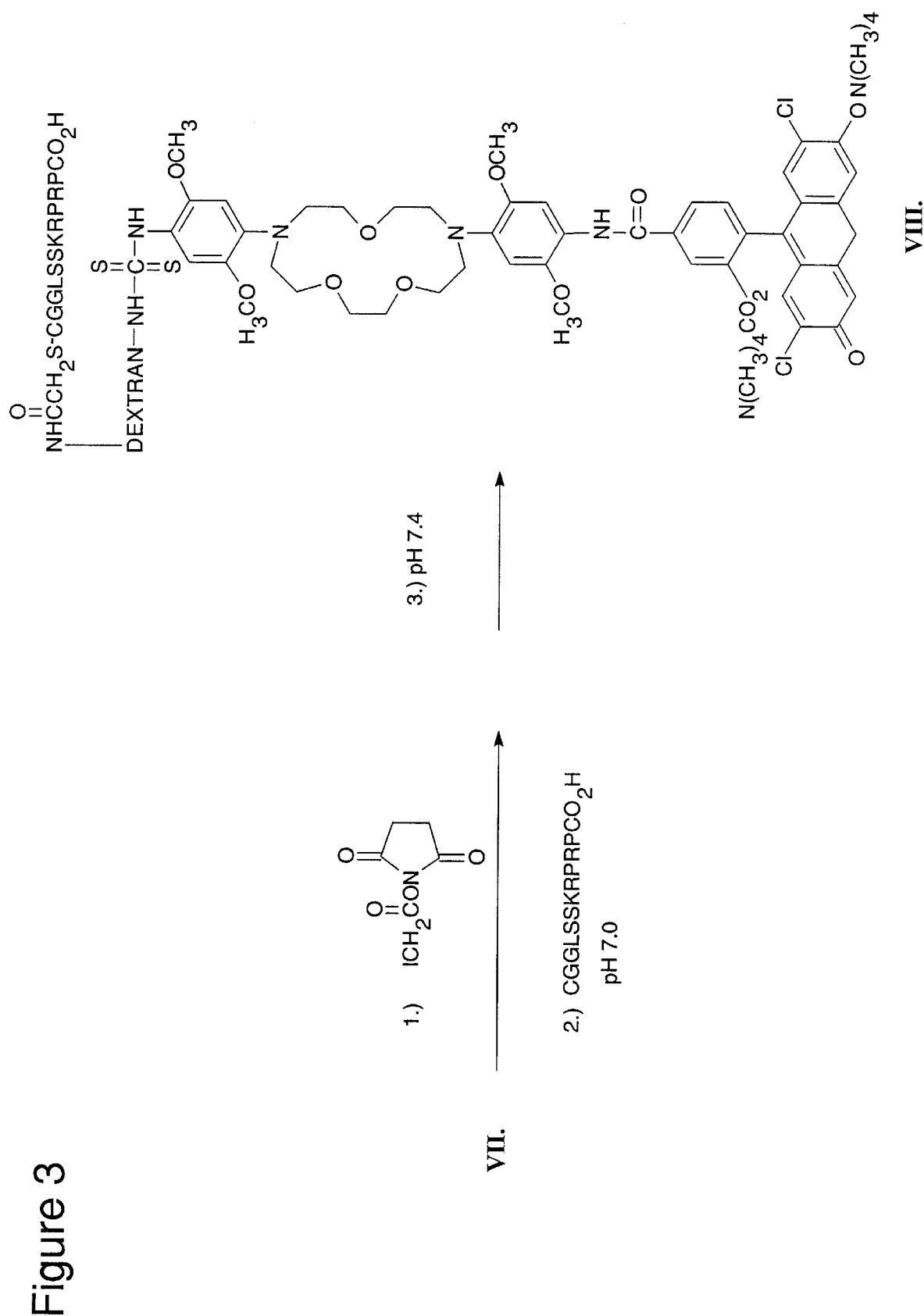
FIG. 3: Conjugation of multiple nuclear localization sequences to a polysaccharide labeled with green fluorescent diaryldiazatrioxa crown ethers.
Figure 4:
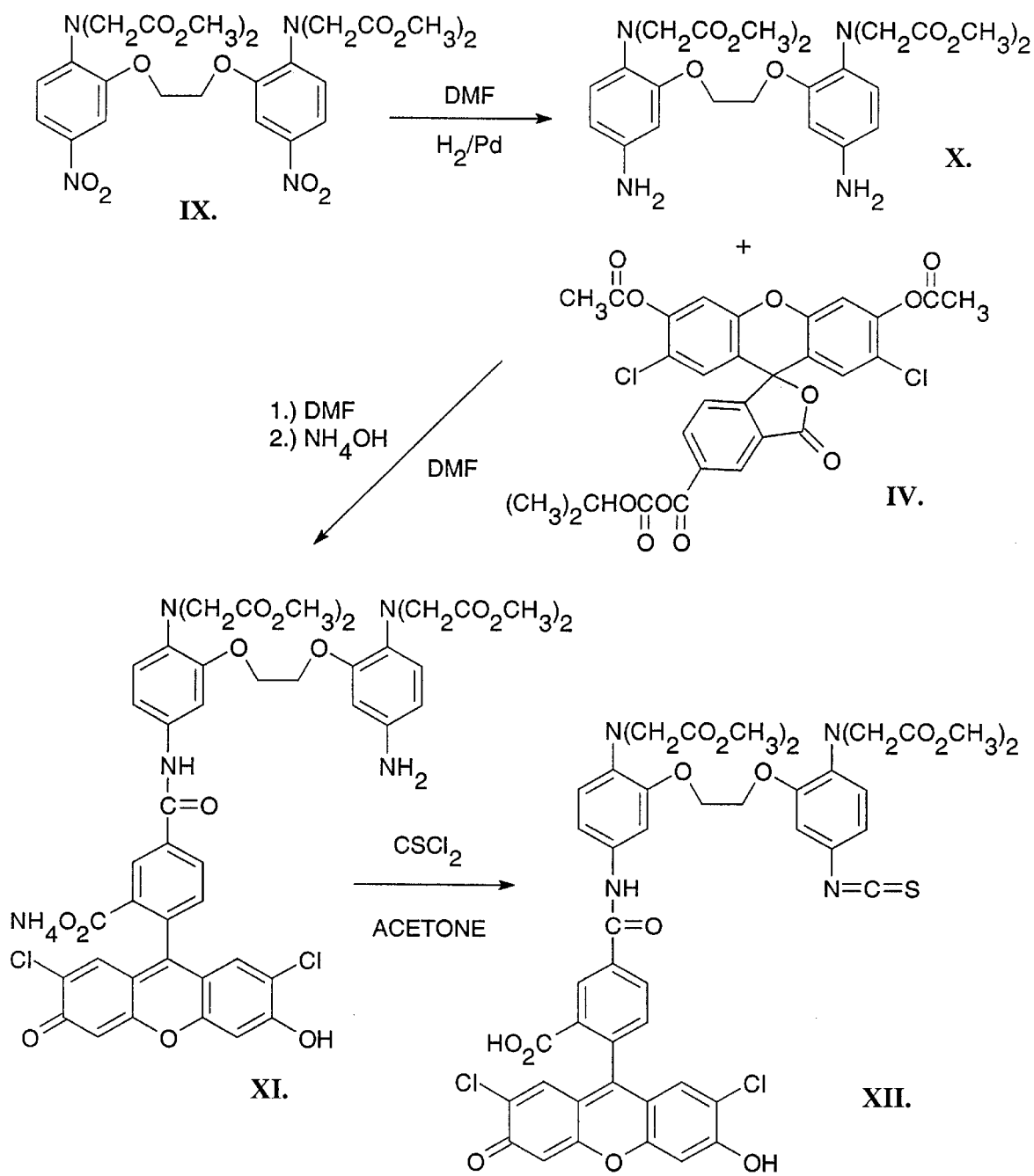
FIGS. 4 and 5: Synthetic pathway to a bifunctional, calcium indicating dextran containing at least one green fluorescent calcium indicator based on 2',7'-dichlorofluorescein and at least one nuclear localization peptide.
Figure 5:
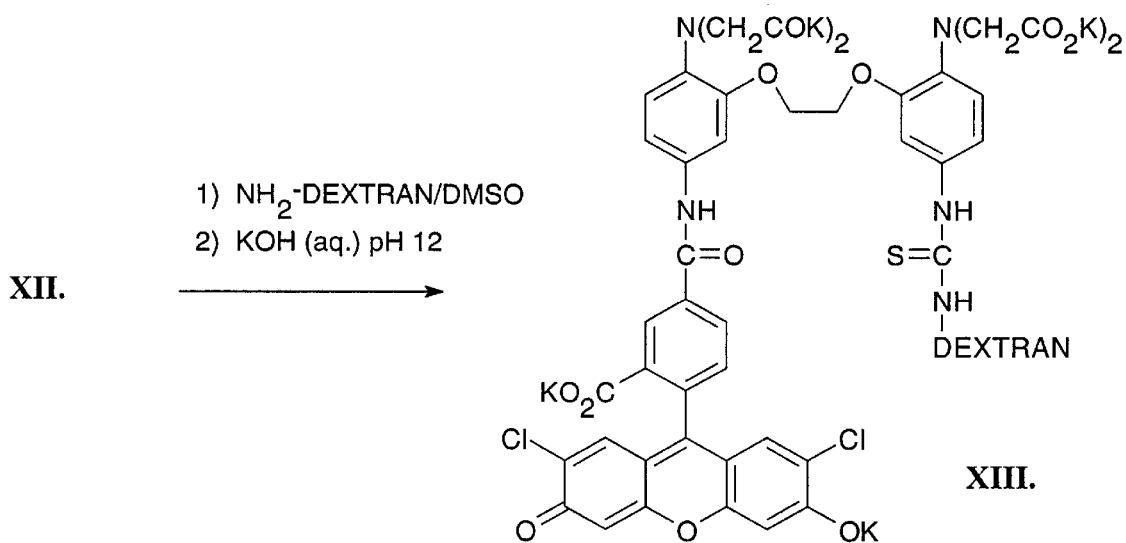
Figure 5:
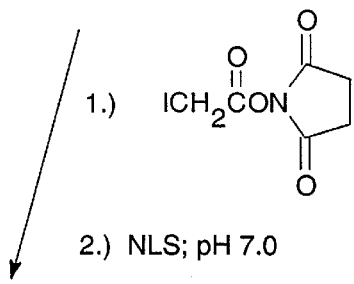
Figure 5:
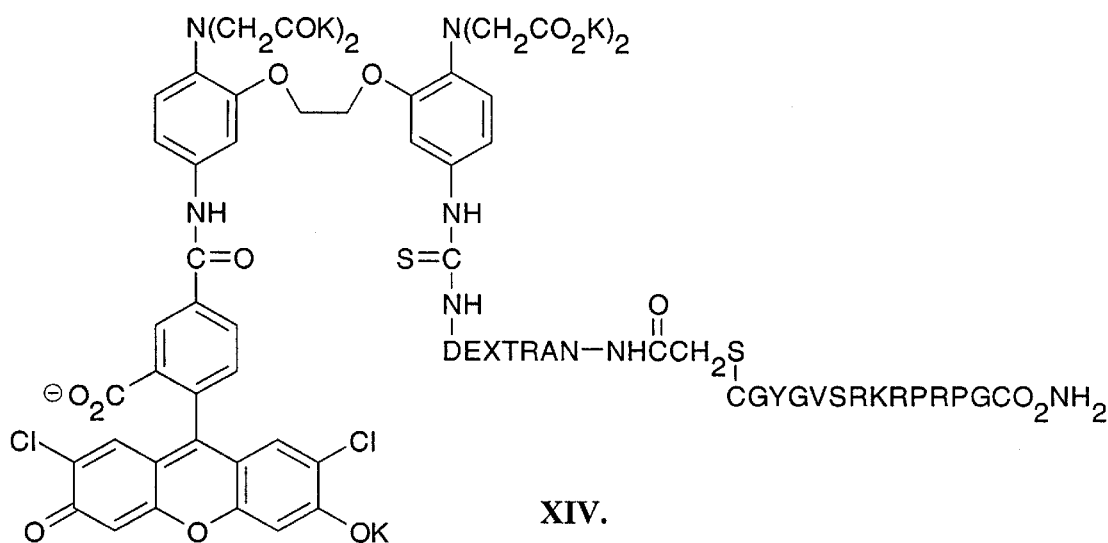

This invention comprises a method for measuring or regulating metal ion concentrations in specific cellular regions or substructures. A necessary element of the invention is the assembly of a bifunctional polysaccharide, which is bound to both a targeting peptide and a chelating moiety, where the chelating moiety is optionally fluorescent. The bifunctional polysaccharide can therefore be described in three parts: the polysaccharide polymer, the chelating moiety, and the targeting peptide.

The Polysaccharide

The polysaccharide polymer useful for the invention is a natural or chemically modified water-soluble polysaccharide that is optically transparent. Transparency is defined has having a low intrinsic absorbance at wavelengths between 350 nm and 800 nm. Suitable polysaccharides are water soluble dextran, ficol, heparin, glycogen, amylopectin, mannan, inulin, starch, agarose and cellulose. All of these polysaccharides are readily available at low cost, high purity, low background absorbance and fluorescence and have relatively uniform physical properties. Preferred embodiments of the invention utilize dextrans or ficols, most commonly dextrans.

The polysaccharide has an average molecular weight of greater than about 1,000 Daltons. Typically, the average molecular weight of the polysaccharide is also less than about 10,000,000 Daltons. The molecular weight of polymers is almost always polydisperse. The lower limit insures that the polysaccharide will be retained within the cell. To reduce light scattering, the polysaccharide preferably has an average molecular weight that is less than about 3,000,000 Daltons. Preferred molecular weight ranges for materials targeted to cell nuclei are between about 3,000 and about 1,500,000 Daltons.

The Chelating Moiety

The chelating moiety is a portion of the novel materials that displays high selectivity for a particular mono- or divalent metal ion. Selectivity is defined as preferentially binding to a specific ion within the expected physiological concentration range of that ion. A chelator is considered selective if it has at least a ten-fold discrimination against competing ions. Preferably selectivity of the chelator moiety is fifty-fold discrimination. More preferably, selectivity of the chelator moiety is greater than 100-fold discrimination against competing ions, at the expected physiological concentration range. In one embodiment of the invention, the chelator moiety binds preferentially and with selectivity for alkali or alkaline earth metal ions. Preferably the chelator binds to biologically important ions such as $Ca^{2+}$, $Mg^{2+}$, $Na^+$, $K^+$, or $Li^+$. In one aspect of the invention, the chelator is non-fluorescent and binding of the ion to the chelator is used to regulate the intracompartmental levels of the bound ion. In another aspect of the invention, the chelator moiety of the compound is attached to a fluorophore moiety and functions as an indicator of intracompartmental levels of the bound ion.

When the chelating moiety functions as an indicator, it contains a fluorescent moiety (FLUOR) attached to the chelating moiety. The fluorescent moiety exhibits a change in spectral properties upon binding the metal ion in the chelate. The change in spectral properties of the fluorophore is generally enhanced absorbance, enhanced emission, a discrete shift in the excitation band, or a discrete shift in the emission band, or any combination thereof. Typically the fluorescent moiety is a xanthylium, 2-indolyl, coumarin, or benzofuran fluorophore. The xanthylium, 2-indolyl and coumarin fluorophores are bound to the indicator by a single covalent bond, or an ether, thioether, urea, thiourea, sulfonamide, carboxamide, or alkylamine linkage, as in Table I. Benzofuran fluorophores are bound to the indicator by sharing two aromatic ring carbons (forming a fused ring system).

As used herein, a xanthylium fluorophore includes substituted or unsubstituted xanthylium dyes, which are fluorescent compounds that contain at least three fused 6-membered rings, where the center ring contains an oxygen heteroatom. Xanthylium dyes have the aryl substituent typically found in these fluorophores (e.g. in fluorescein, rhodamine, etc.) or it is optionally absent. The xanthylium dyes, including the aryl-substituted xanthylium dyes, are typically substituted by one or more amino or hydroxy substituents and are optionally fused to one or more additional aromatic rings that may, in turn be substituted by one or more amino or hydroxy substituents. Amino substituents may be substituted by lower alkyl substituents with <5 carbons or incorporated in saturated heterocyclic rings that are fused to the xanthylium dyes such as in rhodamine 101. Additional permitted substituents on the xanthylium moiety, which may be the same or different, include hydrogen, halogen, carboxy, sulfo, alkyl, perfluoroalkyl, alkoxy and carboxyalkyl (each with <7 carbons). Examples of xanthylium derivatives include, but are not limited to pyronines, xanthenes, fluoresceins, rhodamines, rosamines, rhodols, benzofluoresceins, dibenzofluoresceins, seminaphthofluoresceins and naphthofluoresceins and their substituted derivatives.

Chemically reactive, commercially available xanthylium fluorophores that are useful in synthesizing the compounds of this invention are described in Haugland, HANDBOOK OF FLUORESCENT PROBES AND RESEARCH CHEMICALS (1992) (incorporated by reference), and include, among others, fluorescein-5-isothiocyanate; tetramethylrhodamine-6-isothiocyanate; 5-carboxyfluorescein; 5-carboxytetramethylrhodamine; 5-carboxy rhodol derivatives (and other rhodol derivatives described in U.S. Pat. No. 5,227,487, incorporated by reference); rhodamine 101 sulfonyl chloride (Texas Red™ of Molecular Probes, Inc., OR); 5-carboxy-2',7'-dichlorofluorescein; 5-carboxyseminaphthofluorescein; 5-carboxynaphthofluorescein; 5-(dichlorotriazinyl) aminofluorescein; eosin-5-iodoacetamide; 5-bromomethylfluorescein; fluorescein-5-maleimide; 5-aminofluorescein; and Lissamine rhodamine B sulfonyl cadaverine.

The 2-indolyl fluorophore, as used herein, includes substituted 2-indolyl fluorophores, that may be further substituted by a carboxy group or a pharmaceutically acceptable salt. As used herein, pharmaceutically acceptable salt means non-toxic salts of carboxylic acids known and used in the pharmaceutical industry. Examples include $K^+$, $Na^+$, $Cs^+$, $Li^+$, $Ca^{2+}$, $Mg^{2+}$, $NR_4^+$ salts, where R=H, $C_1$–$C_4$ alkyl, or $C_2$–$C_4$ alkanol or combinations thereof, or combinations of acid salts of these counterions plus free acid groups.

Coumarin fluorophores, as used herein, include substituted coumarins. The coumarin fluorophores include, but are not limited to, coumarins, hydroxycoumarins, alkoxycoumarins, dialkylaminocoumarins, and trifluoromethylcoumarins.

Benzofuran fluorophores, as used herein, include substituted benzofuran fluorophores, that may be substituted by a heteroaryl group, i.e. an aromatic group that contains at least one heteroatom (a non-carbon atom forming the ring structure). A ring can be a 5- or 6- member ring. The heteroaryl group can be a single ring structure or a fused 2- or 3-ring structure. The heteroaryl group can contain one or more heteroatoms, e.g. pyrrole, thiophene, or furan (single ring, single heteroatom), or oxazole, isoxazole, oxadiazole, or imidazole (single ring, multiple heteroatoms), or benzoxazole, benzothiazole, or benzimidazole, (multi-ring, multiple heteroatoms), or benzofaran or indole (multi-ring, single heteroatom). The heteroaryl group may contain additional substituents, which may be the same or different, and may be hydrogen, halogen, carboxy, sulfo, alkyl, perfluoroalkyl, alkoxy or carboxyalkyl (each with <7 carbons), or a pharmaceutically acceptable salt.

Preferred derivatives of the invention have a single fluorophore for each chelating site and preferably have a fluorescence quantum yield of at least 0.1 in either the bound or unbound state, and an extinction coefficient above 20,000 $cm^{-1}$ $mol^{-1}$. More preferred derivatives have a quantum yield of at least 0.4 in either the bound or unbound state, and an extinction coefficient above 70,000 $cm^{-1}$ $mol^{-1}$.

Embodiments of the chelating group of the invention, suitable for the complexation of $Na^+$, $K^+$, or $Li^+$, contain a diaryldiaza crown ether moiety of the structure:

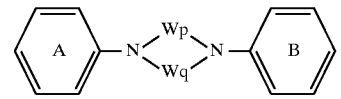

where $W_p$ is $-[CH_2CH_2O]_j-CH_2CH_2-$ and $W_Q$ is $-[CH_2CH_2O]_k-CH_2CH_2-$, and j and k are independently 1 or 2. The crown ethers of this invention are named as follows: diaza[number of ring atoms]crown-number of non-carbon ring atoms. Therefore, the smallest possible crown is diaza[12]crown-4, and the largest is diaza[18]crown-6. The appropriate crown ether for detecting lithium ions is diaza[12]crown-4, the appropriate crown ether for detecting sodium ions is diaza[15]crown-5, and the appropriate crown ether for detecting potassium is diaza[15]crown-6.

The polysaccharide portion of the compound (described above) is linked to substituted aryl B by a single covalent bond, or a covalent linkage as described below. The remaining substituents on rings A and B, which may be the same or different, are independently H, $CH_3$, $NO_2$, $CF_3$, F, Cl, Br, I, $-OR^5$, $-(C=O)OR^5$, or $-OCH_2(C=O)OR^5$, where $R^5$ is H, an alkyl group with about 1–6 carbons, or a pharmaceutically acceptable salt. Alternatively, one or more of the remaining A or B substituents, which are optionally the same or different, is a fluorescent moiety (FLUOR) that exhibits a change in spectral properties upon binding the metal ion in the chelate. Typically FLUOR is a xanthylium fluorophore, a 2-indolyl fluorophore, a coumarin fluorophore, or a benzofuran fluorophore, linked to the substituted aryl A.

The key intermediates in synthesis of the chelating conjugates are N,N'-diaryldiaza crown ethers containing appropriate substituents for attachment or formation of the linking groups, reactive groups and fluorophores. Several methods exist for synthesis of these intermediates: 1. modification of known N,N'-diaryl crown ethers; 2. modification of known diaza crown ethers in which both nitrogen atoms are substituted by hydrogen; 3. complete synthesis of the crown ether from appropriately-substituted anilines (U.S. Pat. No. 5,405,975 to Kuhn et al. (1995), incorporated by reference).

In one embodiment of the invention, nitration and subsequent reduction of substituted diaryl-diaza crown ethers is used to introduce two aromatic amine functions on the chelate. In one preferred embodiment, the two N-phenyl rings are each substituted with two methoxy groups (Examples 1 and 2). After nitration and reduction, one of the resulting amines is modified with a fluorescent reporter molecule, preferably with an excitation wavelength greater than 450 nm and a quantum yield of at least 0.1 in aqueous solution (e.g. 5-carboxy-2', 7'-dichlorofluorescein; Example 3). The second amine is converted to a reactive isothiocyanate which is coupled directly to an amine labeled dextran. This fluorescent dextran conjugate is selective for Na$^+$ ion in the millimolar range (Example 7). Reacting the remaining free amines on the dextran with a heterobifunctional cross-linking reagent introduces reactive sites on the dextran that can be coupled with a reactive site on the target peptide. In one preferred embodiment of the invention, the bifunctional cross-linking reagents consist of an amine-reactive succinimidyl ester and a thiol-reactive iodoacetamide, which are reacted with the amine groups on a dextran to introduce thiol-reactive sites. The modified dextran is then reacted with a cysteine residue on the targeting peptide, as in Example 6.

In another embodiment of the invention, a chelating compound with selectivity for Ca$^{2+}$ contains a BAPTA-based tetracarboxylate moiety of the structure:

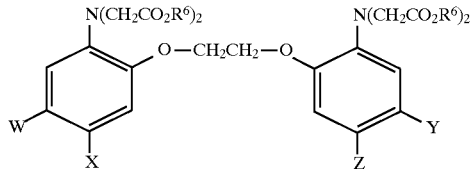

where R$^6$ is either H, or a pharmaceutically acceptable salt. The chelating moiety is bound to the polysaccharide at one of W and X by a single covalent bond, or a covalent linkage as described below.

The remainder of substituents W, X, Y, and Z, which may be the same or different, are independently H, CH$_3$, NO$_2$, CF$_3$, F, Cl, Br, I, —OR$^5$, —CO$_2$R$^5$, or —OCH$_2$CO$_2$R$^5$, where R$^5$ is H, an alkyl group with 1–5 carbons, or a pharmaceutically acceptable salt. Alternatively, one or more of the remaining substituents W, X, Y, and Z, which are optionally the same or different, is a fluorescent moiety (FLUOR) that exhibits a change in spectral properties upon binding the metal ion in the chelate. Typically, FLUOR is a xanthylium fluorophore, a 2-indolyl fluorophore, a coumarin fluorophore, or a benzofuran fluorophore. In one embodiment of the invention, one of X and Z is a xanthylium fluorophore, a 2-indolyl fluorophore, or a coumarin fluorophore. Alternatively, Y taken together with Z and the aromatic carbons at the 4' and 5' positions form a benzofuran fluorophore.

Figure 11:
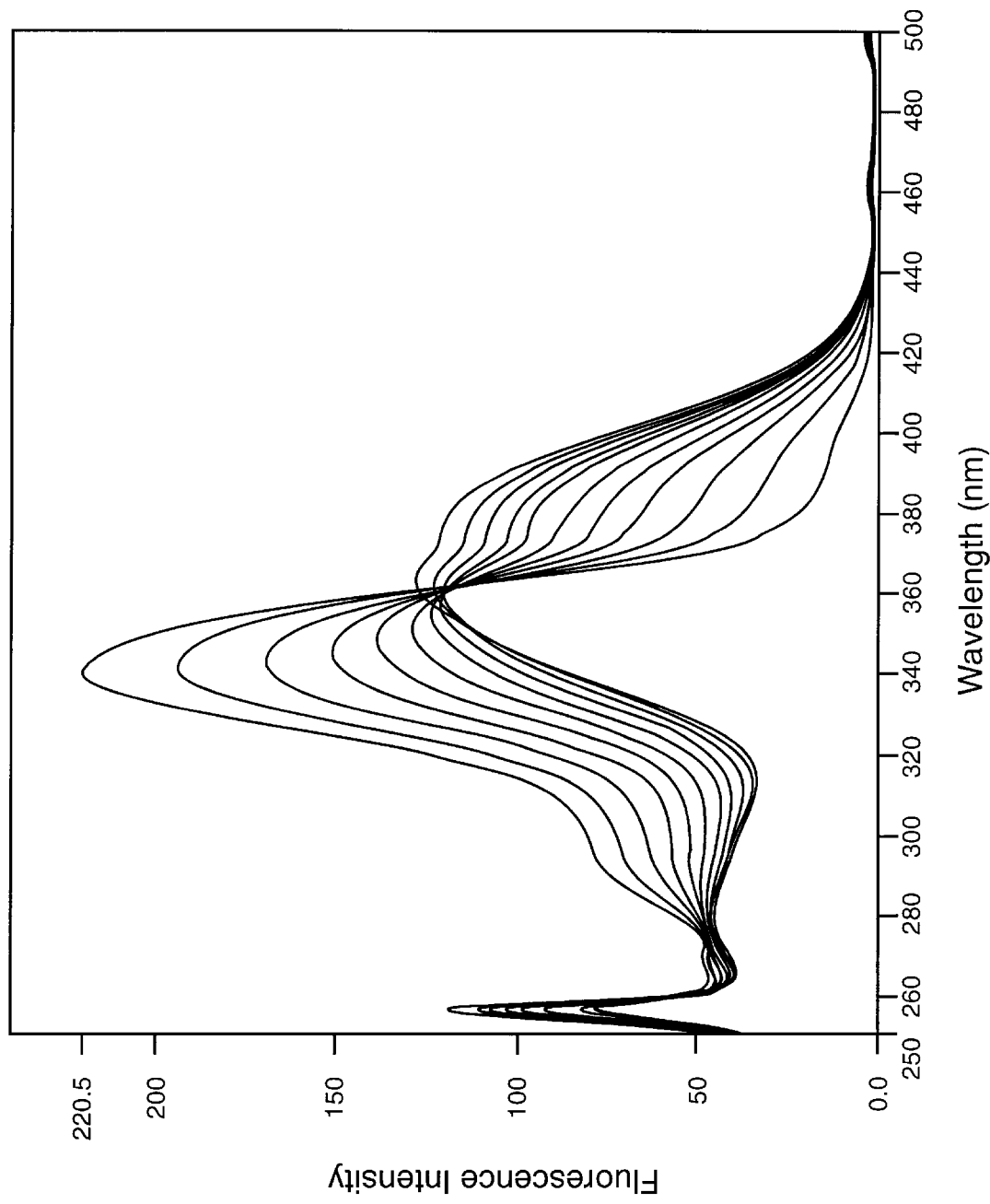
FIG. 11: Fluorescence response of a green fluorescent, $Ca^{2+}$-selective indicator based on an oxazolyl-furan conjugated to a polysaccharide (Compound XX). $Ca^{2+}$ concentrations range from zero to 35 $\mu$M as described in Example 20.
Figure 12:
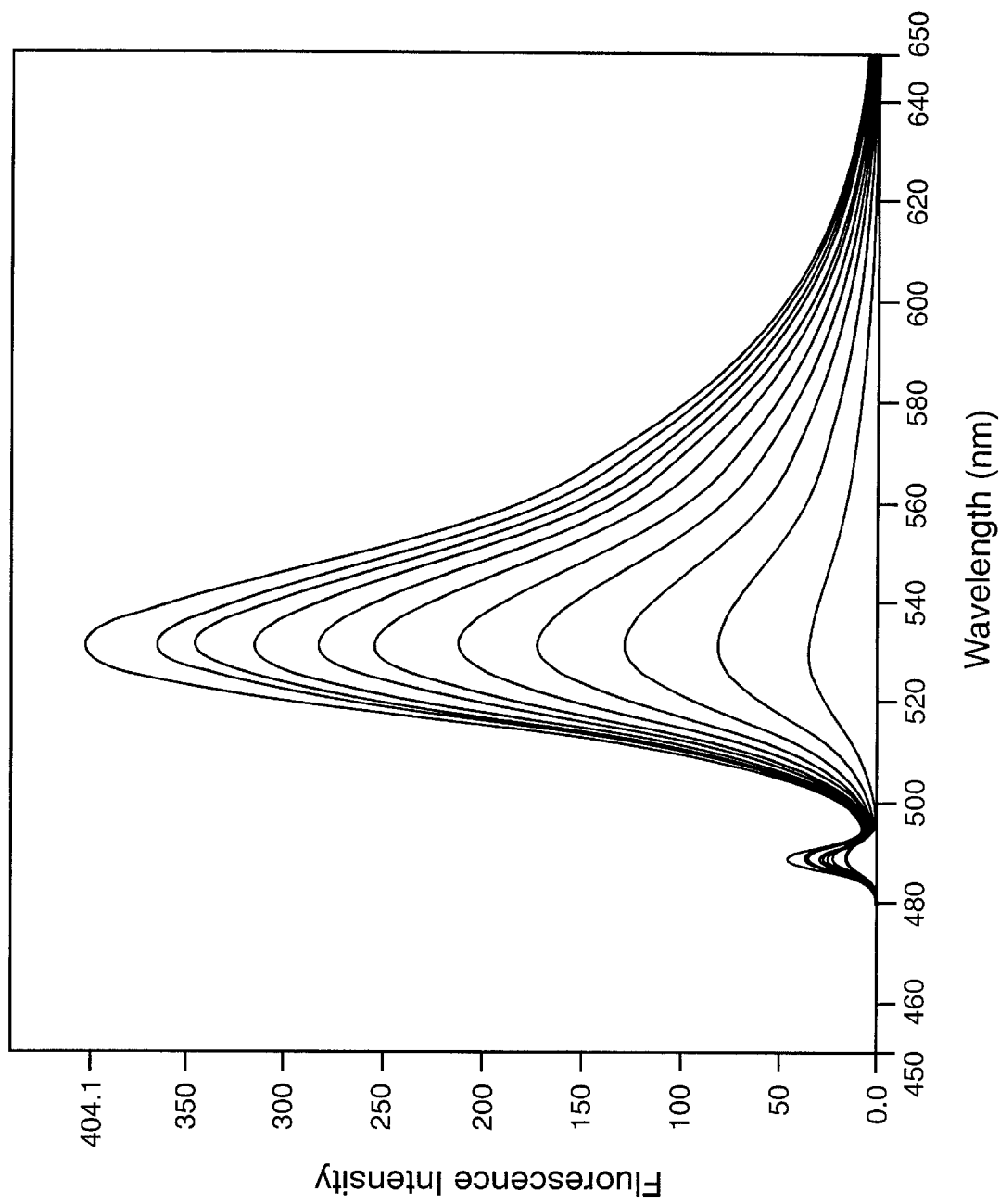
FIG. 12: Fluorescence response of a green fluorescent, $Ca^{2+}$-selective indicator based on 2',7'-dichlorofluorescein conjugated to a polysaccharide (Compound XIII). Samples are excited at 488 nm and the emission scanned between 450 nm and 650 nm. The method used is identical to that described in Example 20.

In preferred embodiments, the Ca$^{2+}$ selective indicator contains one reporter fluorophore for every chelating site. In order to form a covalent attachment to a polysaccharide, the indicator is modified at some point during the synthesis to include a reactive site or masked reactive site, which can then be used to conjugate the indicator to a polysaccharide. By one method, a nitro group is introduced into the indicator and is subsequently reduced to an amine. The amine can then be converted to an amine-reactive isothiocyanate by treatment with thiophosgene, as in Example 14. The indicator can then be coupled to an amino-substituted polysaccharide to give a fluorescent ion-indicating conjugate which responds to changes in Ca$^{2+}$ levels (Example 18; FIG. 11).

Another embodiment of the chelating moiety of the invention, suitable for the analysis of Mg$^{2+}$, contains an APTRA-based tricarboxylate moiety of the structure:

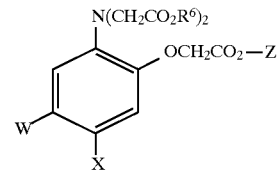

where R$^6$ is either H or a pharmaceutically acceptable salt. The polysaccharide is bound to the indicator at one of W, X or Z by a single covalent bond, or a covalent linkage as described below. The remaining substituents of W and X is H, CH$_3$, NO$_2$, CF$_3$, F, Cl, Br, I, —OR$^5$, —CO$_2$R$^5$, or —OCH$_2$CO$_2$R$^5$, where R$^5$ is H, an alkyl group with 1–5 carbons, or a pharmaceutically acceptable salt. Alternatively, W or X is bound to a fluorescent moiety (FLUOR) that exhibits a change in spectral properties upon binding the metal ion in the chelate. FLUOR is typically a xanthylium fluorophore, a 2-indolyl fluorophore, a coumarin fluorophore, or the substituents at W and X and the aromatic carbons at the 4 and 5 positions may form a benzofuran fluorophore. If Z is not the polysaccharide, Z is H or a pharmaceutically acceptable salt.

Preferred embodiments for Mg$^{2+}$ indicators based on the APTRA structure include derivatives attached to the polysaccharide through a carbomethoxy group such as the blue fluorescent indolyl derivative described in Example 20.

The Targeting Peptide

The targeting peptide is a peptide that is, by virtue of its composition or sequence, recognized by receptors or proteins on a specific intracellular membrane, resulting in transport of the compound attached to the targeting peptide across the intracellular membrane. Any peptide sequence that functions to localize the bifunctional polysaccharide preferentially in a cellular region or substructure can be used to practice the invention. The peptide typically contains one to several amino acids in addition to the sequence used to accomplish localization. Typically the targeting peptide contains a nuclear localization peptide, a mitochondrial localization peptide, or an endoplasmic reticulum localization peptide. A number of localization peptides are known in the art, e.g. Garcia-Bustos, et al., BIOCHIM. BIOPHYS. ACTA 1071, 83 (199 1) (incorporated by reference); Harti, et al., BIOCHIM. BIOPHYS. ACTA 988, 1 (1989) (incorporated by reference); Hendrick, et al, PNAS 86, 4056 (1989) (incorporated by reference); Munro, et al., CELL 48, 899 (1987) (incorporated by reference). Examples of nuclear localization peptides include Cys Gly Tyr Gly Val Ser Arg Lys Arg Pro Arg Pro Gly (SEQ ID NO:1); Cys Gly Gly Pro Lys Lys Lys Arg Lys Val Gly (SEQ ID NO:2); Cys Gly Orn Ala Lys Lys Lys Lys Leu Asp (SEQ ID NO:3); Cys Val Arg Thr Thr Lys Gly Lys Arg Lys Arg lie Asp Val (SEQ ID NO:4); Cys Gly Gly Leu Ser Ser Lys Arg Pro Arg Pro (SEQ ID NO:5). Mitochondrial targeting peptides often contain the sequence R-Xaa-(F)-Xaa-Xaa-(S) (SEQ ID:6) within the amino-terminal 50 amino acids, where R=Arg; Xaa=other amino acid; (F) in location three (3) can be phenylalanine, leucine, valine, or isoleucine; and S in location six (6) can be serine, threonine, or glycine. Localization peptides for the endoplasmic reticulum commonly share the carboxyl terminus sequence Lys Asp Glu Leu (SEQ ID NO: 7).

The above references support our assertion that additional targeting sequences that serve essentially the same function in these and other organelles are likely to exist and that the targeting sequences may be incorporated into larger peptides or proteins, while retaining their essential function of resulting in subcellular localization of the species to which they are attached.

Peptides of any amino acid composition can now be made synthetically, and several university facilities and commercial suppliers now prepare peptides of any desired sequence less than about 50 amino acid residues long. Appropriate reactive groups such as cysteine or lysine, or unnatural amino acids can be introduced into these sequences prior to conjugation to polysaccharides. Methods for attachment of peptides to proteins are well-documented in the art, in particular for production of antibodies to peptides. Analogous methodologies can be used to attach peptides to polysaccharides.

Covalent Linkage

The linking groups between the chelating group and the polysaccharide, and between the targeting peptide and the polysaccharide, are formed by reacting functional groups on the indicator and peptide sequence with appropriate functional groups on the polysaccharide. Table 1 lists many of the functional groups that can be used to form the linkages, and the groups with which they typically react. The tabulation is not all inclusive since with the appropriate choice of solvent, temperature and catalysts, other functional groups can be made to react. Alternative equivalent functional groups will be obvious to one skilled in the art. Preferred embodiments include carboxamide, urea, and thiourea linkages, which utilize the amino functional groups present on commercially available aminodextran, or the carboxylic acid on carboxylated dextrans. Additional ways to activate dextrans for stable coupling to nucleophiles on the peptide or chelator include use of cyanuric chloride, epoxides, cyanogen bromide and a variety of sulfonyl halides such as tresyl chloride.

TABLE 1

FUNCTIONAL GROUPS

| FUNCTIONAL GROUPS (attached to chelator or peptide) | REACT WITH: (on polysaccharide) | TO YIELD: (linkage) |
| --- | --- | --- |
| alcohols/phenols | alkyl halides | ethers |
| haloacetamides | thiols | thioethers |
| maleimides | thiols | thioethers |
| alkyl halides | thiols | thioethers |
| alkyl sulfonates | thiols | thioethers |
| alkyl halides | alcohols/phenols | ethers |
| alkyl sulfonates | alcohols/phenols | ethers |
| thiols | sulfonate esters | thioethers |
| thiols | haloacetamides | thioethers |
| thiols | maleimides | thioethers |
| thiols | epoxides | thioethers |
| amines/anilines | sulfonyl halides | sulfonamides |
| amines/anilines | carboxylic acids | carboxamides |
| amines/anilines | anhydrides | carboxamides |
| amines/anilines | activated esters* | carboxamides |
| amines/anilines | alkyl halides | alkyl amines |
| amines/anilines | isocyanates | ureas |

TABLE 1-continued

FUNCTIONAL GROUPS

| FUNCTIONAL GROUPS (attached to chelator or peptide) | REACT WITH: (on polysaccharide) | TO YIELD: (linkage) |
| --- | --- | --- |
| amines/anilines | isothiocyanates | thioureas |
| amines/anilines | chlorotriazines | aminotriazines |
| amines/anilines | cyanates | cyanamides |
| amines/anilines | sulfonate esters | alkyl amines |
| carboxylic acids | amines/anilines | carboxamides |
| anhydrides | amines/anilines | carboxamides |
| activated esters* | amines/anilines | carboxamides |
| chlorotriazines | amines/anilines | aminotriazines |
| isocyanates | amines/anilines | ureas |
| isothiocyanates | amines/anilines | thioureas |

*Activated esters, as understood in the art, generally have the formula —COΩ, where Ω is a good leaving group (e.g. oxysuccinimidyl (—OC$_4$H$_4$O$_2$), -1-oxybenzotriazolyl (—OC$_6$H$_4$N$_3$); or a phenoxy group or phenoxy substituted one or more times by electron withdrawing substituents such as nitro, fluoro, chloro, cyano, or trifluoromethyl, or combinations thereof, used to form activated phenyl esters; or a carboxylic acid activated by a carbodiimide to form an anhydride or mixed anhydride —OCOR$^8$ or —OCNR$^8$NHR$^9$, where R8 and R9, which may be the same or different, are C$_1$—C$_6$ alkyl, C$_1$—C$_6$ perfluoroalkyl, or C$_1$—C$_6$ alkoxy; or cyclohexyl, 3-dimethylaminopropyl, or N-morpholinoethyl).

Embodiments of the invention contain at least one targeting peptide and at least one chelating moiety covalently bound to the polysaccharide. Preferred embodiments contain more than one targeting peptide and more than one chelating moiety bound to the polysaccharide. More preferred embodiments of the invention contain at least one mole of a chelating group and one mole of a targeting peptide for every 15,000 molecular weight equivalents of polysaccharide (e.g. approximately 0.6 chelating groups or indicators and 0.6 peptides attached to each 10,000 molecular weight polysaccharide or 4.2 chelating groups or indicators and peptides attached to each 70,000 molecular weight polysaccharide molecule). While a polysaccharide containing one targeting peptide per reagent will localize within the targeted cellular substructure, it is understood that the process of localization will be accelerated by linking several copies of the targeting peptide to the polysaccharide.

Method of Use

Bifunctional chelating polysaccharides containing at least one copy of both a peptide-based targeting sequence and a chelating moiety that is optionally fluorescent can be used to reversibly measure or regulate the level of target ion in sub-cellular compartments consisting of an aqueous interior space surrounded by a membrane. These compartments lie inside the aqueous cytoplasm of the cell and take up cytoplasmic proteins containing a peptide sequence recognized by receptors on the sub-cellular membrane. The desired level of target ions in the subcellular structure can be measured or regulated by the use of a chelating polysaccharide of the appropriate molecular weight range that contains a chelating moiety selective for the target ion and a targeting peptide specific for the desired substructure. In one embodiment, regulation of the target ion level comprises maintaining the ion concentrations at a desired level by use of the chelating polysaccharide in an amount sufficient to regulate the ion concentrations. Another embodiment comprises analysis of the ion concentration by detection or quantification of the fluorescent response of a fluorescent chelating polysaccharide.

The polysaccharides are dissolved in water at a concentration of 5 to 50 mg/mL of injection buffer which tries to mimic expected cytoplasmic pH and ion concentration, for example 125 mM KCl, 5 mM NaCl, 20 mM HEPES and 2 mM MgCl$_2$ at pH 7.4.

Generally the bifunctional polysaccharide is introduced into the cytoplasm by pressure microinjection methods. Using a microscope (phase contrast) and micromanipulator, the target cell is pierced with a microinjection syringe and the polysaccharide is introduced directly into the cytoplasm in a pressurized burst. The volume of injected cells must usually be less than 10% of the total cell volume because cells can tolerate only a small increase in volume without disruption of the plasma membrane. In one embodiment, the polysaccharide conjugate is introduced into an egg cell, either before or after fertilization, and the cell is observed during division. The indicator is a vital stain in developing embryos and can be used up to 2 days after injection. The compounds of the invention are also suitable for use with a variety of cultured cells, including rat basophilic leukemia cells, PC12 cells, and primary cultured hippocampal neurons.

Alternative methods of introducing the bulky polysaccharide into the cytoplasm include scrape loading techniques, (short mechanical disruption of the plasma membrane where the plasma membrane is peeled away from the cytoplasm, the dextran perfused through the sample and the plasma membrane reassembled), patch clamp methods (where an opening is maintained in the plasma membrane for long periods) or phagocytosis. Any other treatment that will permeabilize the plasma membrane, such as electroporation, shock treatments or high extracellular ATP can be used to introduce the bulky polysaccharide into the cellular cytoplasm.

Once in the cytoplasmic space, the polysaccharide diffuses throughout the aqueous space and comes into contact with receptors on the surface of the target compartment. The receptors recognize the bifunctional polysaccharide and pull it through the membrane into the sub-cellular compartment, where it selectively binds to the target ion and/or responds to changes in ion levels with a change in fluorescence. Where the polysaccharide is a nuclear-targeted dextran, the polysaccharide conjugate takes approximately 3–20 minutes to localize completely within the nucleus. The exact time required for localization is cell-type dependent.

When regulation of intracellular ion levels is desired, the non-fluorescent chelating polysaccharide should be introduced into the cell in an amount sufficient to maintain the desired level of ion within the target substructure upon localization therein. In addition, where the chelating polysaccharide is being used to buffer ion concentration within a localized region in the cell, the degree of localization can be determined by additional conjugation of the polysaccharide to a non-chelating fluorescent dye, wherein the dye is any fluorophore capable of producing visible fluorescence within the cell. When measurement of the ion levels is desired, the appropriate fluorescent chelating polysaccharide should be introduced into the cell in an amount sufficient to yield a detectable fluorescent response.

Using confocal or epifluorescence microscopy with filters complimentary to the expected wavelengths of response (for example, fluorescein filters are compatible with Compound VII, which is optimally excited at about 530 nm), the dye response is initially observed as an evenly distributed fluorescence, which increases in the target compartment over time. Because of the small volume of the sub-cellular compartments, the dye concentrates in the compartment and gives a very bright signal. Any bifunctional polysaccharide that has not been localized within the target compartment appears as a dim fluorescence throughout the cytoplasm, where it still responds to changes in cytoplasmic levels of the target ion.

Because of the small volume of the nuclear compartment relative to the cytoplasm, the nuclear targeted bifunctional polysaccharides can be used as tracers for cell division without a large degree of dilution. This method of recording nuclear Ca$^{2+}$ levels allows the researcher to perform a separate analysis of Ca$^{2+}$ response for each individual cell.

Quantification of metal ion levels in cellular compartments is accomplished using the fluorescent indicating polysaccharides by ratiometric methods known in the art (Haugland, HANDBOOK OF FLUORESCENT PROBES AND RESEARCH CHEMICALS, 1992, pp., 111–112). While the ratio method can be used to determine concentrations using observation of either the excitation spectra of the indicator, the emission spectra of the indicator, or both, usually the indicator must be calibrated (to compensate for variance in the dissociation constant of the indicator due to ionic strength, viscosity, or other conditions within the cell). To calibrate the indicator, ionophores such as nigericin, gramicidin, A23187 or ionomycin are used. Non-ratiometric analysis can also be accomplished by calibration with a second fluorescent dye present in the cytoplasm.

The examples below are given to as to illustrate the practice of this invention. They are not intended to limit or define the entire scope of the invention.

EXAMPLES

Example 1

Synthesis of a bis-(4-nitro-2,5-dimethoxnohenvl)-diazatrioxa Crown Ether (Compound II)

Compound I (bis-(2,5-dimethoxyphenyl)-diazatrioxa crown ether) (500 mg, 1.02 mmoles) (as described in U.S. Pat. No. 5,134,232 to Tsien, et al.) is dissolved in 2.0 mL glacial acetic acid and 135 mg (2.15 mmoles) 70% HNO$_3$ is added in 25 μL aliquots over two minutes. The reaction forms a nonpolar yellow product with R$_f$=0.5 in ethyl acetate. The reaction is diluted with 50 mL CHCl$_3$ and washed four times with 100 mL deionized water. The brown organic layer is evaporated under reduced pressure to give a thick oil. This is dissolved in 5 mL CHCl$_3$ and purified on 100 mL silica gel (0.04–0.06 mM) that is eluted with 10% ethyl acetate in CHCl$_3$. The pure column fractions are evaporated to a clear yellow oil, which crystallizes on trituration with methanol to give 190 mg (Compound II). The NMR in CDCl$_3$ shows 3.6–3.8 ppm 20H (m); 3.85 ppm 6H (s); 3.95 ppm 6H (s); 7.55 ppm 4H (s).

Example 2

Synthesis of a bis-(4-amino-2,5-dimethoxyohenyl)-diazatrioxa Crown Ether (Compound III).

Compound II (150 mg) is dissolved in 5 mL N,N-dimethylformamide (DMF) and the solution is hydrogenated at 25 psi for two hours. A TLC of the colorless reaction shows complete conversion of II to a polar product that reacts with ninhydrin on TLC to give a blue-colored product. The reaction is filtered to remove the catalyst and the filtrate is diluted to 50 mL with ethyl acetate. The colorless solution is washed three times with 100 mL deionized water and then evaporated under reduced pressure to give 60 mg of a light yellow oil (Compound III) that is >95% pure on TLC in 3% acetic acid/10% methanol/87% chloroform.

Example 3

Synthesis of a Conjugate of bis-(4-amino-2,5-dimethoxyphenyl)-diazatrioxa Crown Ether with One Green Fluorescent Dye (2',7'-dichlorofluorescein) and One reactive amine group (Compound V).

Compound III (50 mg) is dissolved in 3 mL CHCl$_3$ to give a clear solution. 1.0 equivalents of 5-carboxy-2',7'-dichlorofluorescein diacetate isobutyl mixed anhydride (Compound IV) is added as a clear solution in 1.0 mL CHCl$_3$ and the resulting yellow solution is stirred at room temperature for six hours. TLC in 1% acetic acid/10% methanol/89% CHCl$_3$ shows complete conversion of II to a higher R$_f$ product that becomes red on exposure to ammonia vapor. Reaction with ninhydrin gives a ruddy brown product on TLC. The reaction mixture is diluted to 5 mL with CHCl$_3$ and loaded directly onto a silica gel column packed and eluted in 10% methanol in CHCl$_3$. The product is eluted with 1% acetic acid/10% methanol/89% CHCl$_3$ to give 35 mg of the mono-fluorescein conjugate as a colorless oil.

The acetate protecting groups are removed by dissolving the above oil in 2 mL dioxane/methanol (1:1) and adding 15 μL of ammonium hydroxide (30% aqueous). A TLC of the red solution shows conversion to a lower R$_f$, red product with dim green fluorescence. The solvents are removed under vacuum to yield 28 mg of the tetraammonium salt (Compound V) as an opaque red oil.

Example 4
Synthesis of a Conjugate of bis-(4-amino-2,5-dimethoxyphenyl)-diazatrioxa Crown Ether with One Green Fluorescent Dye (2',7'-dichlorofluorescein) and One Reactive Isothiocyanate Group.

Compound V (10 mg) is suspended in 2 mL dry acetone and stirred at room temperature for 30 minutes. 3 μL of thiophosgene is added in one portion; within five minutes all the solid dissolves and the color of the solution changes from red to light brown. TLC in 1% acetic acid/10% methanol/CHCl$_3$ shows complete conversion of the amine to a higher R$_f$ brown/red product that does not react with ninhydrin. The acetone is evaporated under reduced pressure and the resulting brown solid is dried for 12 hours under vacuum to remove traces of thiophosgene to yield 10 mg of the reactive fluorescent crown ether.

Example 5
Synthesis of a Conjugate of bis-(4-amino-2,5-dimethoxyphenyl)-diazatrioxa Crown Ether with One Green Fluorescent Dye (2',7'-dichlorofluorescein) and One Water Soluble Polymer (Compound VI).

100 mg of a 70,000 MW aminodextran (average of 30 amines/dextran) is dissolved in 2 mL DMSO by stirring at room temperature for 30 minutes. Compound VI (10 mg) is dissolved in 0.5 mL DMSO and the light yellow solution added dropwise to the stirring aminodextran solution over three minutes. On addition of the reactive indicator the solution turns bright red with strong fluorescence. The reaction is stirred at room temperature until a TLC shows that over 90% of compound XIV is consumed. The reaction is added to 25 mL of stirring acetone and the orange flocculent suspension is collected by filtration using a fritted glass funnel. The solid is dissolved in approximately 10 mL deionized water and 0.2 mL acetic anhydride is added to the solution while the pH is kept above 8 by addition of 40% tetramethylammonium hydroxide. The pH is adjusted to 8.5 and the red solution is transferred to a presoaked dialysis tubing (MW cutoff of 12–14,000 Daltons). The dextran conjugate is dialyzed versus 1 L deionized water (2×3 hours) and 1 L pH 7.5 tetramethylammonium hydroxide (2×12 hours) to remove any unreacted dye. The orange solution that remains in the dialysis tubing is transferred to a flask, frozen and lyophilized to give 95 mg light red/orange solid (Compound VI). This conjugate responds to changes in sodium concentration with an increase in fluorescence emission intensity and based on an extinction coefficient of 75,000 cm$^{-1}$M$^{-1}$ is labeled with 5.2 dyes/dextran (see Example 8).

Example 6
Conjugation of a Peptide to a Conjugate of bis-(4-amino-2,5-dimethoxyphenyl)-diaryl-diaza-trioxa Crown Ether with One Green Fluorescent Dye (carboxy-2',7'-dichlorofluorescein) and One Water Soluble Polymer (Compound VII).

Compound VII is dissolved in 50 mL of a buffer containing 20 mM HEPES and 100 mM KCl at pH 8.0. Succinimidyl iodoacetate is dissolved in DMSO and mixed 1:1 with the solution of Compound VI in buffer to give a final concentration of 70 μM dextran and 700 μM of the succinimidyl ester. The reaction proceeds for two hours at room temperature and is then dialyzed against a buffer consisting of 10 mM HEPES and 100 mM KCl at pH 7.0 for 10 hours. 5.3 mg of Adenovirus type 2/5 Ela; 282–289 nuclear localization peptide Cys Gly Gly Leu Ser Ser Lys Arg Pro (SEQ ID NO:8) is dissolved in DMSO at a concentration of approximately 22 mg/mL and incubated with the dextran in 2 mL of the 10 mM HEPES and 100 mM KCl at pH 7.0 for 8 hours. The reaction is stopped by the addition of 5% β-mercaptoethanol and is dialyzed against a buffer containing 125 mM KCl, 5 mM NaCl, 20 mM HEPES and 2 mM MgCl$_2$ at pH 7.4 for 12 hours. The resulting sample is concentrated in a Centricon 30 at 3,000 rpm to a concentration of 30–60 mg/mL of dextran (200 μL for 10 mg of dextran). This solution is sufficiently concentrated for injection into cells.

Example 7
Na$^+$Binding Affinity of a Fluorescent Diaryldiaza Crown Ether with two Identical Green Fluorescent Dyes (2',7'-dichlorofluorescein) Attached by Carboxamide Linkages.

The binding affinity of Compound VII for Na$^+$is determined by dissolving a sample of the purified ammonium salt from Example 3 in 3 mL of each of two solutions: solution 1 ("high Na$^+$") consists of 200 mM NaCl and 10 mM MOPS buffer at pH 7.05; solution 2 ("zero Na$^+$") consists of 10 mM MOPS buffer at pH 7.05 in deionized water. Intermediate concentrations of Na$^+$are generated by cross dilution between the two solutions. For example, the emission of the dye in solution 2 is scanned from 500 nm to 650 nm and then 1/100 of the sample is removed and replaced with 1/100 of solution 1 to arrive at a Na$^+$concentration of 2 mM. This is repeated to cover the entire range from zero to 200 mM Na$^+$and the resulting emission intensities are plotted versus the ion concentrations. A least-squares fit used to arrive at the concentration where the indicator is maximally sensitive to changes in Na$^+$concentration. This is the dissociation constant for Na$^+$and is expressed as a concentration. For Compound VII, the K$_d$ for Na$^+$is determined to be 8 mM.

Example 8
Determining the Degree of Labeling for a Water Soluble Diaryldiaza Crown Ether Conjugate with One Green Fluorescent (2',7'-dichlorofluorescein) Dye.

A 50 μL aliquot of the stock solution from Example 7 is diluted into 3 mL of 135 mM KCl, 10 mM MOPS buffer at pH 7.05 the absorption spectra of the two solutions are scanned. The degree of labeling is then calculated by a comparison of the extinction coefficient of the labeled dye at 510 nm with that of free 5-carboxy-2',7'-dichlorofluorescein. In this way, the number of dyes covalently bound to an

Example 9
Synthesis of a BAPTA Tetramethyl Ester that Contains two Reactive Amine Groups (Compound X).

11.0 g (17.7 mmoles) of 5,5'-dinitro BAPTA tetramethyl ester (Compound IX) [Cell Calcium 10, 491 (1989)] is dissolved in 200 mL dimethylformamide and the solution is hydrogenated at 40 psi for three hours in the presence of 0.8 g 10% palladium on charcoal. When complete, the reaction is filtered through diatomaceous earth. The clear filtrate is diluted to 500 mL with ethyl acetate and the solution is washed three times with saturated NaCl and once with water. The organic layer is dried over $Na_2SO_4$ and evaporated under reduced pressure to a gray oil. Trituration with methanol yields 7.0 g (12.4 mmoles; 70.3% yield) of 5,5'-diamino BAPTA, tetramethyl ester (Compound X), ~95% pure by TLC in 5% methanol:$CHCl_3$.

Example 10
Synthesis of a Conjugate of BAPTA Tetramethyl Ester that Contains One Green Fluorescent (2',7'-dichlorofluorescein) Dye Linked by a Carboxamide Linkage and One Reactive Amine Group Compound XI.

5,5'-Diamino BAPTA tetramethyl ester (Compound X) (0.35 g, 0.64 mmoles) is dissolved in 5 mL dichloromethane. One equivalent of the mixed anhydride of 5-carboxy-2',7'-dichlorofluorescein diacetate (Compound IV) (0.43 g, 0.64 mmoles) is added as a solid in three portions over ~10 min. The reaction is stirred at room temperature for three hours, then is stored in an ice bath overnight. TLC using 5% MeOH/$CHCl_3$ shows a new, ninhydrin positive quenching product formed with an $R_f$ of ~0.3, which becomes orange and weakly fluorescent on exposure to ammonia vapors. The mixed anhydride has an $R_f$ of about 0.8 in this solvent and the diamine stays near the origin. Some of each of the starting materials remain. The reaction is loaded directly onto a chromatography column packed with 150 nL silica (40–70 $\mu$) and eluted with 3% MeOH/$CHCl_3$. The purest fractions are combined and evaporated to a cream colored oil. The acetate esters are hydrolyzed by stirring overnight with 5% ammonium hydroxide in 3:1 dioxane:methanol. The precipitate that forms is filtered. Analysis by TLC shows it to contain ~85% of the desired product and about ~15%) product containing two dyes. The solid is dissolved in $CHCl_3$ containing ~15% MeOH and purified on 100 mL silica (40–70$\mu$) packed and eluted in 1% AcOH:10% MeOH:$CHCl_3$. The product is eluted with 1% AcOH to give 285 mg (43% yield) the tetramethyl ester of amino BAPTA containing a single 2',7'-dichlorofluorescein dye (Compound XI).

Example 11
Synthesis of a Conjugate of BAPTA Tetramethyl Ester that Contains One Green Fluorescent (2',7'-dichlorofluorescein) Dye Linked by a Carboxamide Linkage and One Reactive Isothiocyanate Group (Compound XII).

The tetramethyl ester of BAPTA isothiocyanate containing a 2',7'-dichlorofluorescein dye (Compound XII) is synthesized by treating a suspension of 0.13 g (0.13 mmoles) of Compound XI in 10 mL acetone with 10 $\mu$L (0.14 mmoles) thiophosgene for 30 minutes at 30° C. The light yellow solution gives two products $R_f$~0.9 and $R_f$~0.5 in 1% AcOH:9% MeOH:$CHCl_3$. Both products are nearly colorless. The solution is evaporated to a light oil. This is washed with 10 mL methanol. The insoluble solid is centrifuged to give a tan pellet which is redissolved in $CHCl_3$ and evaporated to 125 mg (88% yield) of the lower $R_f$ product (Compound XII), which reacts with n-butyl amine to give a new product on TLC.

Example 12
Preparation of a Conjugate of BAPTA with One Green Fluorescent (2',7'-dichlorofluorescein) Dye Linked by a Carboxamide Linkage and a Water-soluble Polymer Linked by a Carboxamide Linkage (Compound XIII).

The fluorescent BAPTA isothiocyanate tetramethyl ester (Compound XII) (30 mg; 0.028 mmoles) is dissolved in 1 mL dimethylforramide. This solution is added in one portion to a stirring solution of 0.18 g (2.6 $\mu$moles) 70,000 MW amino dextran (approximately 30 moles of amines/70,000 g of dextran, Molecular Probes, Inc.; Eugene Oreg.) in 2 mL DMSO. The dextran is warmed slightly to give a clear solution. The isothiocyanate is light yellow until it reacts with the dextran, when it becomes very red and fluorescent. The reaction is stirred overnight at room temperature. The crude conjugate is added to 100 mL vigorously stirring acetone. The solid is filtered through a fritted glass funnel and the red solid is redissolved in 10 mL deionized water.

The methyl esters are hydrolyzed by adjusting the pH of the dextran solution to 12.5 for 14 hours. The solution is neutralized with HCl to pH 8.0 and dialyzed against deionized water for three days using a 12–14,000 MW cutoff dialysis membrane. The solution is lyophilized to give 0.16 g (2.3 $\mu$moles, 89% yield) of an orange solid (Compound XIII).

Example 13
Conjugation of a Peptide to a Conjugate of BAPTA with One Green Fluorescent (2',7'-dichlorofluorescein) Dye Linked by a Carboxamide Linkage and a Water-soluble Polymer Linked by a Carboxamide Linkage (Compound XIV)

The Calcium Green dextran conjugate (Compound XIII; Example 12) (10 mg) is dissolved in 50 mL of a buffer containing 20 mM HEPES and 100 mM KCl at pH 8.0 to give final concentration of 143 $\mu$M dextran. Succinimidyl iodoacetate is dissolved in DMSO and mixed 1:1 with the solution of dextran in buffer to give a final concentration of 70 $\mu$M dextran and 700 $\mu$M of the succinimidyl ester. The reaction proceeds for two hours at room temperature and is then dialyzed against a buffer consisting of 10 mM HEPES and 100 mM KCl at pH 7.0 for 10 hours. 4.4 mg (20 molar equivalents) of polyoma large T nuclear targeting peptide with a C-terminal cysteine-Cys Gly Tyr Gly Val Ser Arg Lys Arg Pro Arg Pro Xaa (SEQ ID NO:9) is dissolved in 200 $\mu$L of a buffer containing 10 mM HEPES and 100 mM KCl at pH 7.0 and incubated with the dextran in 2 mL of the 10 mM HEPES and 100 mM KCl at pH 7.0 for 8 hours. The reaction is stopped by the addition of 5% β-mercaptoethanol and is dialyzed against a buffer containing 125 mM KCl, 5 mM NaCl, 20 mM HEPES and 2 mM $MgCl_2$ at pH 7.4 for 12 hours. The resulting sample is concentrated in a Centricon 30 at 3,000 rpm to a concentration of 30–60 mg/mL of dextran (200 $\mu$L for 10 mg of dextran). This solution is sufficiently concentrated for injection into cells.

Example 14
Synthesis of a Reactive BAPTA Tetramethyl Ester with One Green Fluorescent (oxazolyl-furan) Dye and a Reactive Amine Group (Compound XIX).

Figure 6:
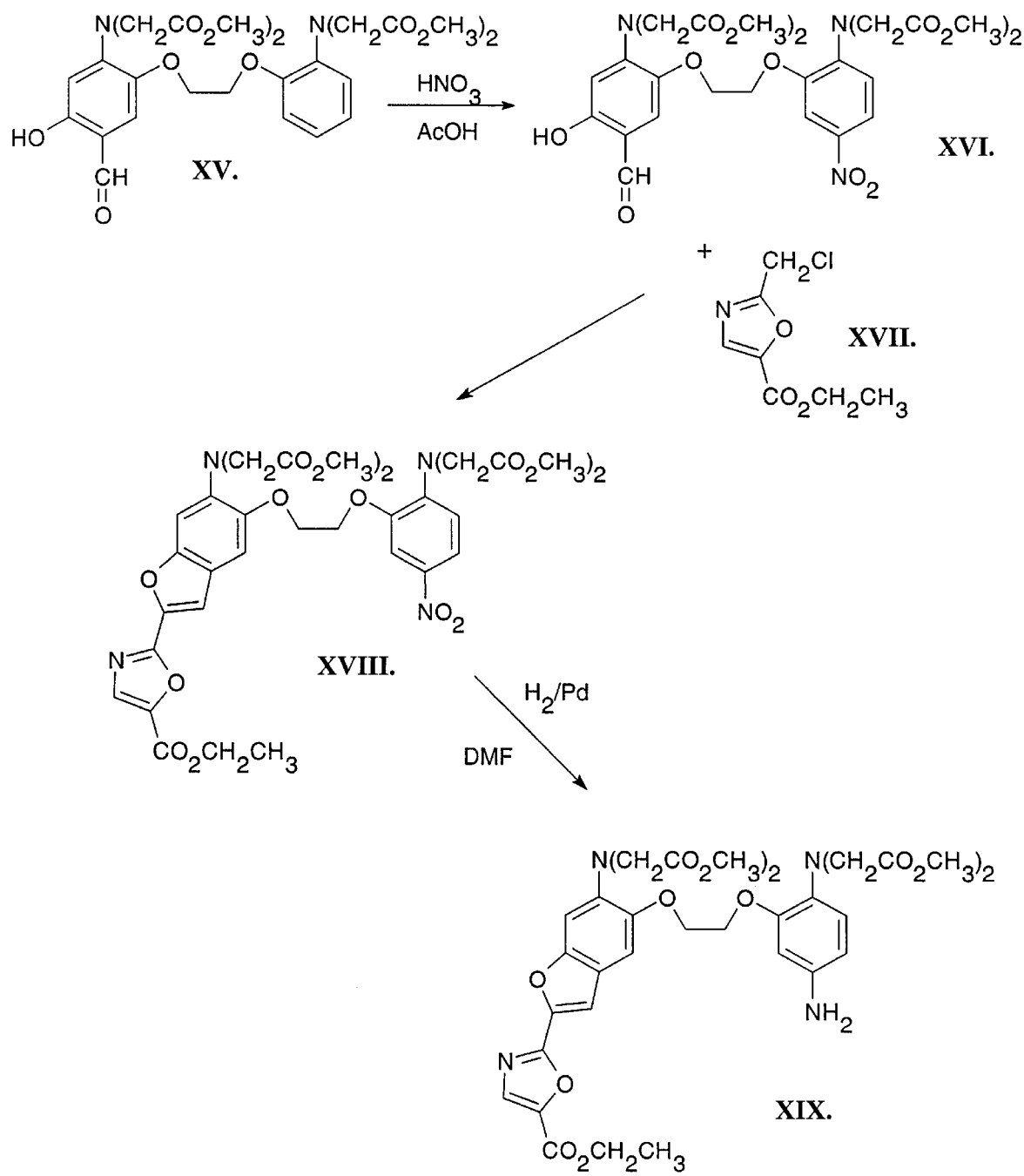
FIGS. 6 and 7: Synthetic pathway to a bifunctional, calcium indicating dextran containing at least one green fluorescent calcium indicator based on an oxazolyl-furan and at least one nuclear localization peptide.
Figure 7:
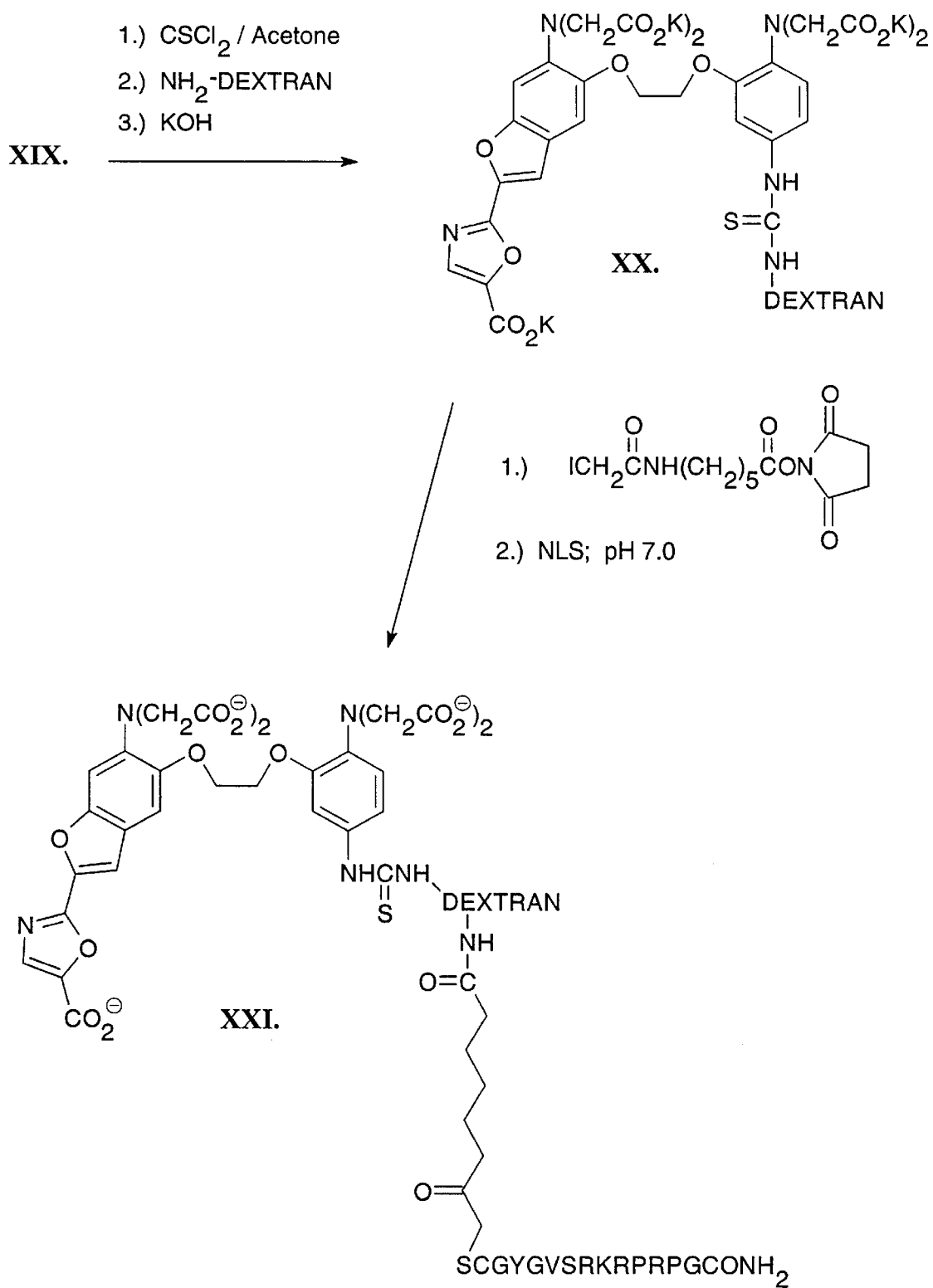
Figure 8:
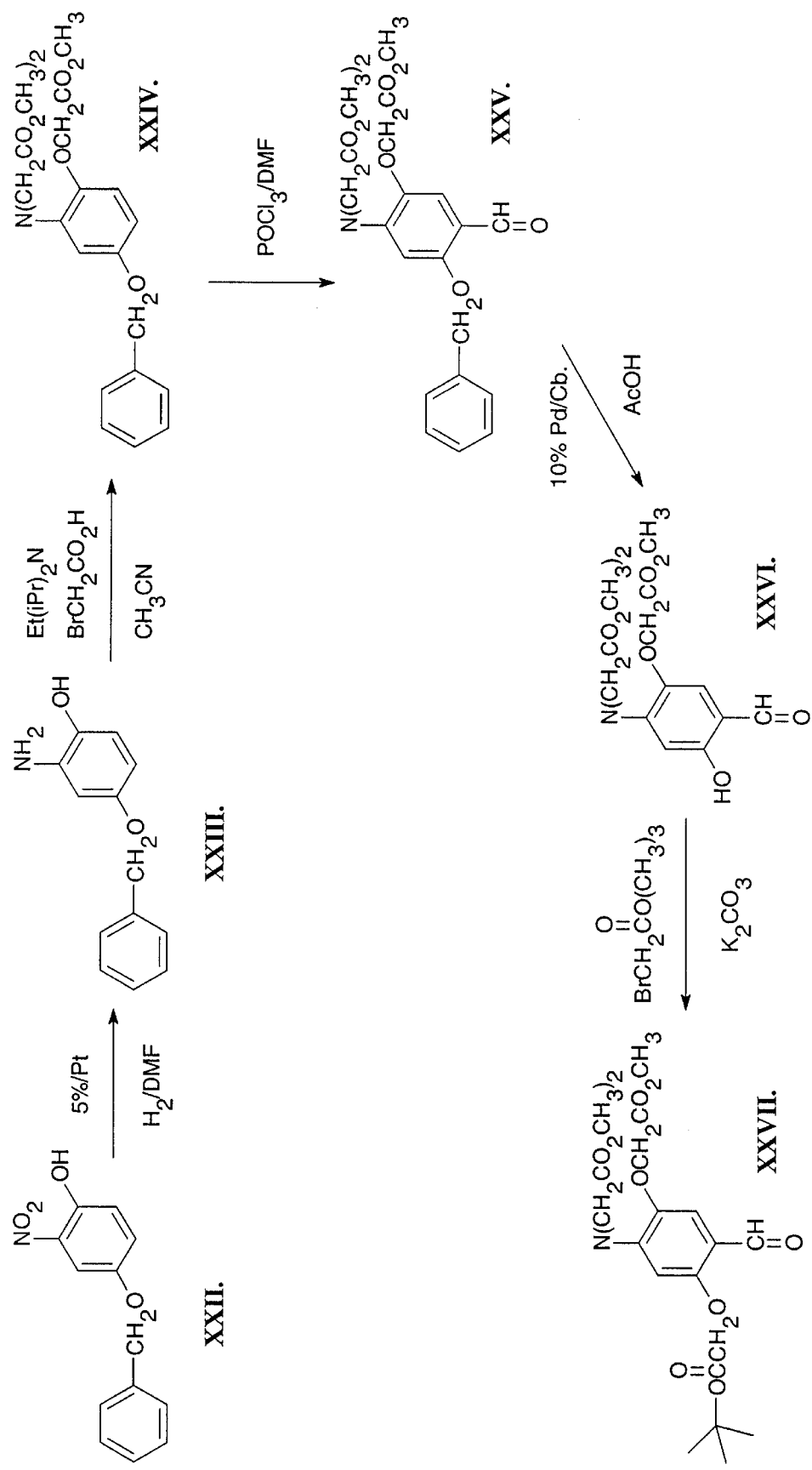
FIGS. 8 and 9: Synthetic pathway to an amine-reactive, magnesium-selective blue fluorescent indicator based on a substituted indolyl-aminophenol-N,N,O-triacetic acid (APTRA).
Figure 9:
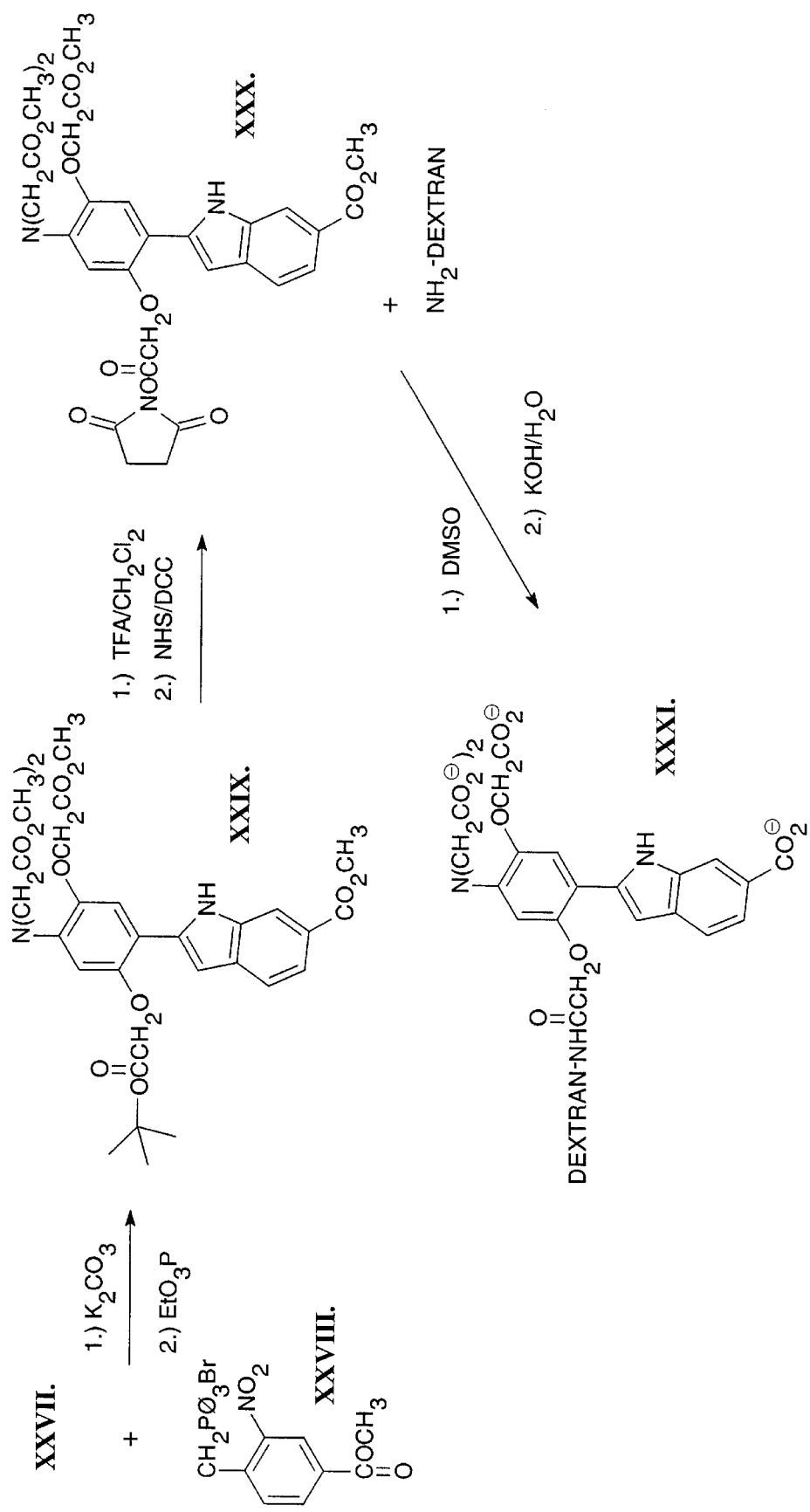
Figure 10:
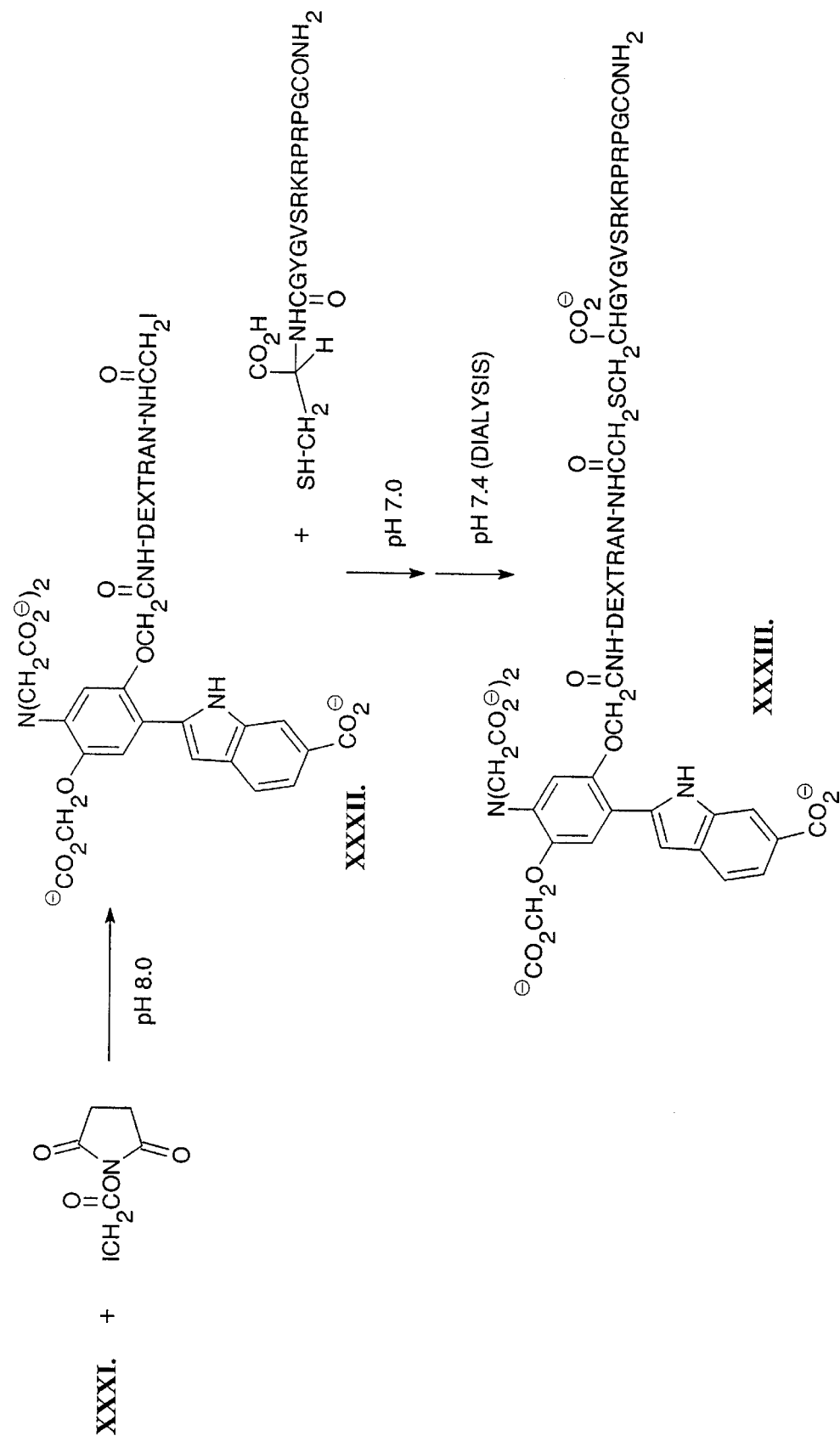
FIG. 10: Synthetic pathway to a bifunctional dextran containing at least one magnesium selective, blue fluorescent indicator based on a substituted indolyl-APTRA and at least one nuclear localization peptide.

The precursor to an appropriately-protected reactive amine analog of the common $Ca^{2+}$ indicator fura-2 is synthesized by a route analogous to that used to prepare fura-2 in U.S. Pat. No. 4,603,209 except that the 5'-methyl group in fura-2 is replaced by the reactive amino group as follows. 2.0 g (3.47 mmoles) of 4-hydroxy-5-formyl BAPTA tetramethyl ester (XV in FIG. 6) is dissolved in 30 mL warm AcOH. This product is nitrated by reaction with 0.27 g (4.17 mmoles) 70% nitric acid that is added dropwise over ~5 min. TLC in 1:1 ethyl acetate:hexanes shows that all the starting BAPTA has been converted to a lower $R_f$, yellow-colored product. The reaction is poured into 150 mL of cold water, stirred for 1 hour and filtered to give 1.7 g of a brown solid (79% crude yield) after drying overnight under vacuum. This material is purified on 150 mL of 45–90µ silica gel packed in and eluted with 1:1:1 EtOAc:CHCl$_3$:hexanes. Pure factions are combined and evaporated to a light yellow oil. This crystallizes on washing with methanol to give 0.89 g (41% yield) of pale yellow crystals of 4-hydroxy-5-formyl-5'-nitro BAPTA tetramethyl ester (Compound XVI).

4-Hydroxy-5-formyl-5'-nitro BAPTA tetramethyl ester (Compound XVI) (0.5 g, 0.8 mmoles) is dissolved in 2 mL dry dimethylformamide and warmed to dissolution. Potassium carbonate is added followed by 0.18 g (0.88 mmoles) 2-chloromethyloxazole-5-carboxylic acid, ethyl ester (Compound XVII). The reaction is heated to 106° C. for 1.5 hours at which point TLC analysis (1:1 ethyl acetate:hexanes) shows good conversion to the slightly blue fluorescent, yellow-colored product. The solution is diluted with 100 mL EtOAc and washed three times with 100 mL brine and once with 100 mL water. The organic layer is evaporated under reduced pressure to a yellow-brown oil. This is heated to boiling with 30 mL methanol for two minutes. Yellow crystals (370 mg; 60% yield) of "5'-nitro-fura" ethyl ester tetramethyl ester (Compound XVIII) form after cooling overnight.

Hydrogenation of 175 mg (0.45 mmoles) Compound XVIII in 5 mL dimethylformamide over 0.05 g 10% palladium on charcoal for two hours gives a clear solution with blue fluorescence. TLC (10% methanol:90% CHCl$_3$) shows complete conversion of the nitro compound to a lower $R_f$, fluorescent product that reacts on heating with ninhydrin. The reaction is filtered through diatomaceous earth to remove the catalyst, the solution is evaporated and the product is crystallized from 7 mL methanol to give 120 mg of tan-gray crystals of "5'-amino fura" ethyl ester tetramethyl ester (73% yield). The product (Compound XIX) is pure on TLC (10% methanol/CHCl$_3$).

Example 15
Synthesis of a Reactive BAPTA Tetramethyl Ester with One Green Fluorescent (oxazolyl-furan) Dye and a Reactive Isothiocyanate Group
Compound XIX (100 mg, 0.138 mmoles) is dissolved in 3.5 mL acetone with slight heating to give a dark gray solution. Thiophosgene (13 µL, 0.16 mmoles) is added to give a gray-green solution. TLC (1:1 EtOAc:hexanes) after stirring for 1.5 hours shows that no amine remains. The product is precipitated with hexanes at 0° C. Fura ethyl ester tetramethyl ester isothiocyanate is filtered the next day to give 83 mg (79% yield) gray crystalline solid, pure by TLC.

Example 16
Preparation of a Conjugate of BAPTA Linked to One Green Fluorescent (oxazolyl-furan) Dye and a Water-soluble Polymer by a Thiourea Linkage (Compound XX).
80 mg (0.104 mmoles) of the amine reactive isothiocyanate from Example 16 is dissolved in 1 mL dimethylformamide to give a yellow solution which is added dropwise over ~1 minute to a solution of 650 mg ~40,000 MW amino dextran containing ~11 amines/mole dextran dissolved in 3 mL DMSO. After stirring the reaction overnight at room temperature the TLC in 10:10:2:0.2 CHCl$_3$:methanol:water:acetic acid shows all fluorescence remains at the origin. The product is precipitated by addition to 100 mL of acetone with stirring. The yellowish precipitate is filtered then redissolved in a minimum volume of deionized water (~15 mL). The esters are hydrolyzed and the product is isolated as described in Example 12. The final dialysis is against pH 7.5 KOH in deionized water to ensure that the counterion is uniformly potassium. The dialysis solution is then lyophilized to give 0.60 g of Compound XX as a yellowish solid.

Example 17
Conjugation of a Peptide to a Water Soluble BAPTA Conjugate with One Green Fluorescent (oxazolyl-furan) Dye XXI
4.7 mg of polyoma large T nuclear localization sequence with a C-terminal cysteine is conjugated to 10 mg of the fura dextran (Compound XX; Example 16) as described in Example 13. Succinimidyl iodoacetate was replaced by another heterobifunctional cross-linking reagent, succinimidyl 6-((iodoacetyl)amino)hexanoate (SIAX, Molecular Probes, Inc. Eugene Oreg.). This results in an additional 6 atom spacer between the peptide and the dextran amine. The product is isolated by lyophilization to a cream colored powder with a mass of 11 mg (Compound XXI).

Example 18
Calcium Binding Affinity of a Water Soluble BAPTA Conjugate with One Green Fluorescent (oxazolyl-furan) Dye.
The affinity of a fluorescent BAPTA compound conjugate is determined by dissolving 5 mg of the labeled dextran (Compound XX) in 1 mL deionized water and diluting 50 µL into three milliliters each of the Calcium Calibration Buffer Kit II (Molecular Probes Inc, Eugene, Oreg.) based on a method described in Methods in Enzymology 172, 230 (1989). For example, 5 mg Compound XX is dissolved in deionized water and 5 µL diluted into three milliliters of each of two buffers, which are cross diluted to arrive at a series of Ca$^{2+}$ concentrations between zero and 35 µM. The excitation of the dye solutions are scanned between dilutions from 250 nm to 500 nm while collecting the emission at 510 nm. The resulting excitation response is similar to that of the free fura-2 (FIG. 11). The change in excitation intensity at either 340 nm or 360 nm can be plotted against the concentration of free Ca$^{2+}$ to give a value for the dissociation constant of the indicator. Alternatively, one can plot the change in the 340/360 excitation ratio to arrive at the dissociation constant of the indicator.

Example 19
Determining the Degree of Labeling for a Water Soluble BAPTA Conjugate with One Green Fluorescent (oxazolyl-furan) Dye.
A 50 µL aliquot of the stock solution from Example 19 is diluted into three milliliters of each of the two Calcium buffers as in Example 38 and the absorption spectra of the two solutions are scanned. The degree of labeling is then calculated by a comparison of the extinction coefficient of the labeled dye with that of the free dye. In this way, the number of dyes covalently bound to an average molecular weight dextran can be determined. The degree of substitution of the dextran conjugate synthesized in Example 17 (Compound XX) is 4.2 dyes/40,000 MW dextran.

Example 20
Synthesis of a Conjugate of APTRA Trimethyl Ester with One Blue Fluorescent (indolyl) Dye and a Carboxylic Acid and its Succinimidyl Ester (Compound XXX).

50 g. 4-benzyloxy-2-nitrophenol [U.S. Pat. No. 4,603,2091] (Compound XXII) is dissolved in 100 mL dimethylformamide to give a yellow solution which is shaken in the presence of 5% platinum on charcoal under 40 psi pressure of hydrogen. After 12 hours, the reduction is colorless and is filtered through diatomaceous earth to remove the catalyst. The clear filtrate is diluted to 800 mL with ethyl acetate and is washed three times with 500 mL water. The organic layer is evaporated to yield a clear oil, which is triturated with cold methanol and filtered to give 4-benzyloxy-2-aminophenol as a gray solid (Compound XXIII).

After drying for two days under vacuum, Compound XXIII is dissolved in 300 mL acetonitrile and 5.5 molar equivalents of N-ethyl-diisopropylamine and methyl bromoacetate are added. The reaction is stirred 72 hours at reflux. Thin layer chromatography in 1:1 ethyl acetate:hexanes shows complete conversion of the aminophenol to a higher $R_f$ quenching product. The reaction is diluted to 2 L with chloroform and washed three times with pH 2 phosphoric acid. The tan organic layer is evaporated to a thick oil, which recrystallizes from methanol (500 mL) as a gray-white solid (Compound XXIV). NMR analysis shows that this is the desired aminophenol-triacetic acid (4-benzyloxy-APTRA).

The 4-benzyloxy-APTRA (20 gm) is dissolved in 200 mL dry DMF and 1 molar equivalent of triethylamine is added while the reaction stirs under nitrogen. In a separate flask, 75 mL dry DMF is stirred under nitrogen and 3 molar equivalents (based on the APTRA) of phosphorous oxychloride is added dropwise over 30 minutes with cooling in ice. When the addition is complete, the reaction warms to room temperature and becomes dark red. This solution is added dropwise to the stirring solution of Compound XXV in DMF and the reaction is stirred at room temperature for 24 hours to give a thick brown oil. The reaction is poured over 1 L of crushed ice, neutralized with 25% sodium hydroxide to pH 7 and the resulting yellow solid is filtered and washed with water. The solid is triturated with cold methanol and filtered to give a cream-colored solid with a dim blue-purple fluorescence on TLC (Compound XXV; 4-benzyloxy-5-formyl-APTRA).

To remove the benzyl group, Compound XXV (5 gm.) is dissolved in 25 mL glacial acetic acid and warmed to give a solution. 0.5 gm of 10% palladium on charcoal is added and the reaction is put under hydrogen pressure while still warm. The reaction shakes under hydrogen for three hours until TLC in ethyl acetate: hexanes (1:1) shows complete conversion of Compound XXVI to a slightly lower $R_f$, dim green fluorescent product. The reaction is filtered to remove the catalyst and the light yellow filtrate is evaporated to give a thick oil, which crystallizes on trituration with room temperature methanol. Compound XXVI, 4-hydroxy-5-formyl-APTRA is isolated as a cream-colored powder with a purity of 95% by TLC.

Compound XXVI is dissolved in 50 mL dimethylformamide containing 11.6 g (84 mmoles) potassium carbonate and 16.5 g (85 mmoles) tert-butyl bromoacetate. The stirred mixture is heated at 70° C. for two hours. The reaction is cooled to room temperature and diluted with 250 mL ethyl acetate. The solution is washed three times with brine and once with water. The organic layer is dried over sodium sulfate and evaporated at reduced pressure to a gray oil. Crystallization from methanol gives 25 g (85% yield) of colorless crystals of 4-(t-butoxycarbonylmethoxy)-5-formyl-APTRA trimethyl ester that is pure by TLC (ethyl acetate:hexanes 1:1).

4-(t-Butoxycarbonylmethoxy)-5-formyl-APTRA, Compound XXVII (25 g, 35.5 mmoles) is reacted with 29 g (53.3 mmoles) 4-methoxycarbonyl benzyltriphenylphosphonium bromide [XIV in U.S. Pat. No. 4,603,209 or Compound XXVIII] by dissolving both in 70 mL dimethylformamide in the presence of 15 g (0.106 mmoles) potassium carbonate and heating to 90° C. for two hours. TLC using ethyl acetate:hexanes (1:1) shows complete conversion of the product to the corresponding colored vinyl derivative. The reaction is cooled, diluted to 300 mL with ethyl acetate, washed three times with brine and once with water. The organic layer is evaporated at reduced pressure to a red oil. This is purified on 350 mL silica gel (40–70μ) prepared in and eluted with ethyl acetate:hexanes:$CHCl_3$ 1:1:1. The pure column fractions are evaporated to a red oil (18.2 g). This oil is dissolved in 50 mL redistilled triethyl phosphite and refluxed for three hours until the solution is nearly colorless. TLC showed complete conversion of the yellow starting product to the colorless, blue fluorescent derivative. The triethyl phosphite is removed under vacuum while the reaction is still near 80° C. The resulting gray oil is recrystallized from boiling methanol and filtered after cooling to yield 15 g of crude product. This is further purified by column chromatography eluting in 1:1:1 ethyl acetate:hexanes $CHCl_3$. Pure fractions are combined, evaporated and triturated with methanol to obtain 4-(t-butoxycarbonylmethoxy)-5-(6-carbomethoxy-2-indolyl)-APTRA tetramethyl ester (Compound XXIX) as a colorless solid, pure to TLC.

The tert-butyl protecting group of 4-(t-butoxycarbonylmethoxy)-5-(6-carbomethoxy-2-indolyl)-APTRA trimethyl ester (Compound XXIX) is removed by dissolving 2.0 g of the t-butyl ester in 20 mL methylene chloride and adding 6 mL trifluoroacetic acid. After stirring the solution at room temperature overnight the TLC shows complete hydrolysis of the t-butyl ester. The reaction is evaporated to a brown oil. This is triturated with 100 mL methanol to give 2.2 g of a moist yellow solid. This is immediately dissolved in 10 mL chloroform and purified on 150 mL silica gel eluted with 10% methanol, 1% acetic acid in chloroform. The pure fractions of 4-(carboxymethoxy)-5-(6-carbomethoxy-2-indolyl)-APTRA tetramethyl ester are combined and evaporated to a clear oil.

The amine reactive succinimidyl ester of 4-(carboxymethoxy)-5-(6-carbomethoxy-2-indolyl)-APTRA trimethyl ester is synthesized from 0.45 g (0.567 mmoles) of the carboxylic acid dissolved in 3.5 mL $CH_2Cl_2$ and 0.13 g (1.13 mmoles) N-hydroxysuccinimide. The reaction is stirred for 30 minutes then 0.23 g dicyclohexylcarbodiimide dissolved in 0.8 mL $CH_2Cl_2$ is added in one portion to the stirring solution. After stirring for 16 hours at room temperature 0.14 g colorless precipitate of dicyclohexyl urea is filtered. The filtrate is evaporated to a colorless semi-solid of 4-(carboxymethoxy)-5-(6-carbomethoxy-2-indolyl)-APTRA trimethyl ester, succinimidyl ester ("protected mag-indo 1 succinimidyl ester;" Compound XXX) that is about 80% pure by TLC.

Example 21

Preparation of a Reactive APTRA with One Blue Fluorescent (indolyl) Dye and a Water-soluble Polymer Linked by an Ether and a Carboxamide Group (Compound XXXI).

A solution of 0.14 g (0.16 mmoles) of the protected mag-indo 1 succinimidyl ester (Example 29) in 4 mL dimethylformamide is added to a solution of 1 g (14.3 μmoles) 10,000 MW amino dextran substituted by ~3 amines/dextran (Molecular Probes, Inc.; Eugene Oreg.) that is dissolved in 10 mL anhydrous DMSO. After stirring for ~24 hours at room temperature the reaction mixture is added to 250 mL rapidly stirring acetone to precipitate the dextran. The cream-colored gel is filtered and redissolved in 40 mL deionized water. The methyl ester protecting groups are hydrolysed by stirring at pH 12.5 KOH for 12 hours. The pH is adjusted to 8.5 and the solution transferred to a dialysis tubing with a 3,000 MW cutoff and dialyzed against pH 7.5 KOH for two days. The solution is lyophilized to a colorless solid (Compound XX).

Example 22

Conjugation of a Localization Peptide to a Water-soluble Polymer Containing an APTRA with One Blue Fluorescent (indolyl) Dye and Linked to the Polymer by an Ether and a Carboxamide Group (Compound XXXIII)

5 mg of the SV40 large T nuclear localization sequence (126–132) with a C-terminal cysteine is coupled to 10 mg of the Mag-indo dextran from Example 22 using the method described in Example 13 to give the bifunctional magnesium-sensitive dextran as a colorless solid (Compound XXIII).

It is to be understood that, while the foregoing invention has been described in detail by way of illustration and example, numerous modifications, substitutions, and alterations are possible without departing from the spirit and scope of the invention as described in the following claims.

What is claimed is:

1. A compound comprising a water-soluble polysaccharide with molecular weight greater than about 1,000 Daltons that is covalently attached to:
   a) at least one chelating moiety selective for a monovalent or divalent metal ion, wherein the chelatinig moiety acts as a fluorescent indicator for the monovalent or divalent metal ion; and
   b) at least one targeting peptide which serves to localize the compound to the inside of a cellular organelle.

2. A compound, according to claim 1, wherein the polysaccharide is a dextran, ficol, heparin, glycogen, amylopectin, mannan, inulin, starch, agarose, or cellulose and has a molecular weight less than about 3,000,000 Daltons.

3. A compound according to claim 1, wherein the monovalent or divalent metal ion is $Na^+$, $K^+$, $Li^+$, $Ca^{2+}$, or $Mg^{2+}$.

4. A compound according to claim 1, wherein the targeting peptide is specific for localization in the nucleus.

5. A compound according to claim 1, wherein the chelating moiety has the formula:

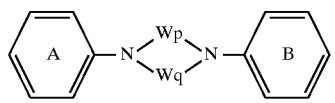

where $W_p$ is $-(CH_2CH_2-O)_j-CH_2CH_2-$ and $W_Q$ is $-(CH_2CH_2-O)_k-CH_2CH_2-$; where j and k are independently 1 or 2, and wherein rings A and B are further substituted;

the polysaccharide is covalently linked to B;

a fluorophore, FLUOR, is covalently linked to A, where FLUOR is a substituted or unsubstituted xanthylium fluorophore, a substituted or unsubstituted 2-indolyl fluorophore, or a substituted or unsubstituted coumarin; and the remaining A and B substituents, which may be the same or different, are independently H, $CH_3$, $NO_2$, $CF_3$, F, Cl, Br, I, $-OR^5$, $-(C=O)OR^5$, or $-OCH_2(C=O)OR^5$, where $R^5$ is H, an alkyl group with about 1–6 carbons, or a pharmaceutically acceptable salt.

6. A compound according to claim 1, wherein the chelating moiety has the formula:

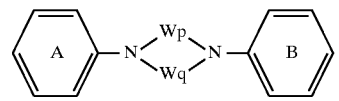

where $W_p$ is $-(CH_2CH_2-O)_j-CH_2CH_2-$ and $W_Q$ is $-(CH_2CH_2-O)_k-CH_2CH_2-$; where j and k are independently 1 or 2, and wherein rings A and B are further substituted;

the polysaccharide is covalently linked to B;

a fluorophore, FLUOR, is linked to A by sharing 2 aromatic carbons as a fused ring, where FLUOR is a substituted or unsubstituted benzofuran fluorophore; and the remaining A and B substituents, which may be the same or different, are independently H, $CH_3$, $NO_2$, $CF_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt.

7. A compound according to claim 1, wherein the chelating moiety has the formula:

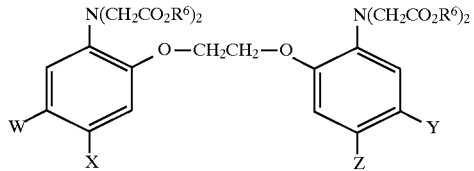

which is covalently bound to the polysaccharide at one of W and X; and one of X and Z is FLUOR, where FLUOR is a substituted or unsubstituted xanthylium fluorophore, a substituted or unsubstituted 2-indolyl fluorophore, or a substituted or unsubstituted coumarin fluorophore; and the remainder of substituents W, X, Y, and Z, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt;

R$^6$ is H, or a pharmaceutically acceptable salt.

8. A compound according to claim 1, wherein the chelating moiety has the formula:

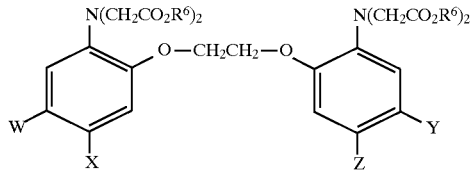

which is covalently bound to the polysaccharide at one of W and X; and wherein Z taken together with Y and the aromatic carbons at the 4' and 5' positions form a benzofuran or oxazolyl-substituted or carboxy-oxazolyl substituted benzofuran fluorophore;

the remainder of substituents W and X, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt; and R$^6$ is H, or a pharmaceutically acceptable salt.

9. A compound according to claim 1, wherein the chelating moiety has the formula:

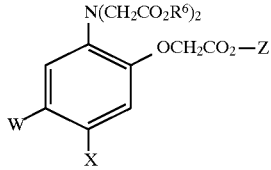

which is covalently linked to the polysaccharide at one of W, X or Z; and if the polysaccharide is not bound at Z, Z is H or a pharmaceutically acceptable salt;

one of W and X is FLUOR, where FLUOR is a substituted or unsubstituted xanthylium fluorophore, a substituted or unsubstituted 2-indolyl fluorophore, or a substituted or unsubstituted coumarin fluorophore;

the remainder of W and X, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt; and R$^6$ is H, or a pharmaceutically acceptable salt.

10. A compound according to claim 1, wherein the chelatinig moiety has the formula:

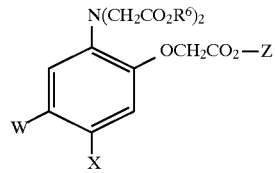

which is covalently linked to the polysaccharide at Z; and

W taken together with X and the aromatic carbons at the 4 and 5 positions form a benzofuran or oxazolyl-substituted or carboxy-oxazolyl substituted benzofuran fluorophore;

R$^6$ is H, or a pharmaceutically acceptable salt.

11. A compound according to claim 1, wherein said polysaccharide is a dextran of molecular weight greater than about 3,000 and less than about 1,500,000;

said chelating moiety has the formula

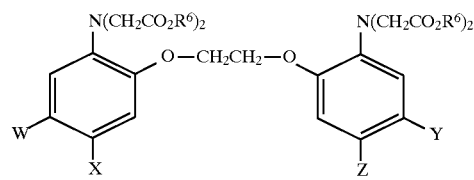

which is covalently bound to the dextran at one of W and X; and one of W and X is FLUOR, where FLUOR is a substituted or unsubstituted xanthylium fluorophore, a substituted or unsubstituted 2-indolyl fluorophore, or a substituted or unsubstituted coumarin fluorophore; or Z taken together with Y and the aromatic carbons at the 4' and 5' positions form a benzofuran or oxazolyl-substituted or carboxy-oxazolyl substituted benzofuran fluorophore;

the remainder of substituents W, X, Y, and Z, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt; and R$^6$ is H, or a pharmaceutically acceptable salt; and said targeting peptide is a nuclear localization peptide of the sequence Cys Gly Tyr Gly Val Ser Arg Lys Arg Pro Arg Pro Gly (SEQ ID NO:1).

12. A method for analyzing intracellular ion levels, comprising:

a) introducing a compound according to claim 1 into the cytoplasm of one or more cells, in an amount sufficient to produce a fluorescent response to physiological levels of a selected mono- or divalent metal ion within a target organelle;

b) incubating the cell or cells for a time sufficient for said compound to localize within the target organelle;

c) observing the fluorescent response of said compound in the target organelle.

13. A method according to claim 12, wherein the chelating moiety has the formula:

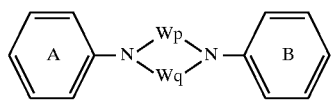

where $W_P$ is —(CH$_2$CH$_2$—O)$_j$—CH$_2$CH$_2$— and $W_Q$ is —(CH$_2$CH$_2$—O)$_k$—CH$_2$CH$_2$—; where j and k are independently 1 or 2, and wherein rings A and B are further substituted;

the polysaccharide is covalently linked to B; and a fluorophore, FLUOR, is attached to A, where FLUOR is a substituted or unsubstituted xanthylium fluorophore, a substituted or unsubstituted 2-indolyl fluorophore, or a substituted or unsubstituted coumarin fluorophore that is covalently linked to A, or FLUOR is a substituted or unsubstituted benzofuran fluorophore linked to A by sharing 2 aromatic carbons as a fused ring;

the remaining A and B substituents, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt.

14. A method according to claim 12, wherein the chelating moiety has the formula:

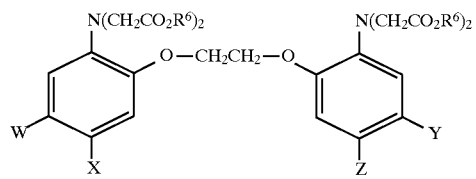

which is covalently bound to the polysaccharide at one of W and X; and one of W and X is FLUOR, where FLUOR is a substituted or unsubstituted xanthylium fluorophore, a substituted or unsubstituted 2-indolyl fluorophore, or a substituted or unsubstituted coumarin fluorophore; or Z taken together with Y and the aromatic carbons at the 4' and 5' positions form a benzofuran or oxazolyl-substituted or carboxy-oxazolyl substituted benzofuran fluorophore;

the remainder of substituents W, X, Y, and Z, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt;

R$^6$ is H, or a pharmaceutically acceptable salt.

15. A method according to claim 12 wherein the chelating moiety has the formula:

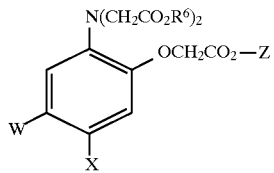

which is covalently linked to the polysaccharide at one of W, X or Z; and if the polysaccharide is not bound at Z, Z is H or a pharmaceutically acceptable salt;

one of W and X is FLUOR, where FLUOR is a substituted or unsubstituted xanthylium fluorophore, a substituted or unsubstituted 2-indolyl fluorophore, or a substituted or unsubstituted coumarin fluorophore; or W taken together with X and the aromatic carbons at the 4 and 5 positions form a benzofuran or oxazolyl-substituted or carboxy-oxazolyl substituted benzofuran fluorophore;

the remainder of W and X, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt;

R$^6$ is H, or a pharmaceutically acceptable salt.

16. A method according to claim 12, further comprising the quantification of the fluorescent response of the compound.

17. A method of detecting nuclear Ca$^{2+}$ levels comprising;

a) introducing into the cytoplasm of a cell having a nucleus, a bifunctional chelating dextran of molecular weight greater than about 3,000 and less than about 1,500,000, where said dextran is covalently attached to one or more nuclear localization peptides of the sequence Cys Gly Tyr Gly Val Ser Arg Lys Arg Pro Arg Pro Gly (SEQ ID NO: 1) and one or more chelating moieties of the formula:

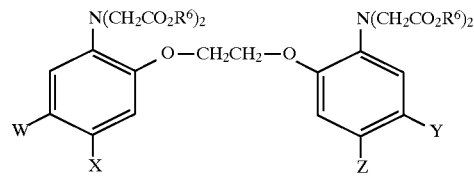

which is covalently bound to the dextran at one of W and X; and one of W and X is FLUOR, where FLUOR is a substituted or unsubstituted xanthylium fluorophore, a substituted or unsubstituted 2-indolyl fluorophore, or a substituted or unsubstituted coumarin fluorophore; or Z taken together with Y and the aromatic carbons at the 4' and 5' positions form a benzofuran or oxazolyl-substituted or carboxy-oxazolyl substituted benzofuran fluorophore;

the remainder of substituents W, X, Y, and Z, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is H, an alkyl group with about 1–6 carbons, or a pharmaceutically acceptable salt; and R$^6$ is H, or a pharmaceutically acceptable salt;

in an amount sufficient to produce a fluorescent response to physiological levels of Ca$^{2+}$ in the nucleus;

b) incubating the cell for a time sufficient for the bifunctional chelating dextran to localize within the nucleus; and c) observing the fluorescent response in the nucleus.

* * * * *